United States Patent [19]
Cameron-Mills et al.

[11] Patent Number: 6,031,155
[45] Date of Patent: Feb. 29, 2000

[54] ARABINOXYLAN DEGRADATION

[76] Inventors: Verena Cameron-Mills, Kirkevaenget 20; Finn Lok, Kongshaven 15, both of Copenhagen—Valby, Denmark, 2500; Catharina Maria Cornelia Sinjorgo, Filips van Almondestraat 24-2, 1057 ZV Amsterdam, Netherlands; Ronald Tako Marinus van den Dool, Dalkruid 1, 4102 KR Culemborg, Netherlands; Martinus Petrus Maria Caspers, Leeuweriklaan 6, 2289 EG Rijswijk, Netherlands; Maria Joanna van Zeijl-van der Valk, Verhoevenstraat 37, 2291 RN Wateringen, Netherlands

[21] Appl. No.: 08/869,696

[22] Filed: Jun. 5, 1997

[51] Int. Cl.[7] .............................. C12N 5/04; C12N 15/29; C12N 15/81; C12N 15/82
[52] U.S. Cl. ...................... 800/284; 435/69.1; 435/69.7; 435/69.8; 435/252.3; 435/254.2; 435/320.1; 435/325; 435/419; 435/468; 435/471; 435/483; 536/23.6; 800/287; 800/298; 800/320
[58] Field of Search .............................. 435/69.1, 320.1, 435/410, 419, 468, 471, 483, 69.7, 69.8, 252.3, 254.2, 325; 536/23.6, 24.1; 800/278, 287, 295, 298, 520, 284

[56] References Cited

U.S. PATENT DOCUMENTS

| | | | |
|---|---|---|---|
| 4,456,550 | 6/1984 | Dvorak et al. | 530/350 |
| 5,194,596 | 3/1993 | Tischer et al. | 530/399 |
| 5,316,921 | 5/1994 | Godowski et al. | 435/69.4 |
| 5,328,837 | 7/1994 | Godowski et al. | 435/69.4 |
| 5,332,671 | 7/1994 | Ferrara et al. | 435/240.1 |
| 5,571,509 | 11/1996 | Comoglio et al. | 435/94.5 |

FOREIGN PATENT DOCUMENTS

| | | | |
|---|---|---|---|
| 0 227 159 A2 | 3/1986 | European Pat. Off. | C12C 9/00 |
| 0 228 732 A1 | 3/1986 | European Pat. Off. | C12P 19/14 |
| WO 91/19782 | 12/1991 | WIPO | C12N 1/15 |
| WO 94/21785 | 9/1994 | WIPO | C12N 9/24 |
| WO 95/23514 | 8/1995 | WIPO | A12D 8/04 |
| WO 96/30525 | 3/1996 | WIPO | C12N 15/56 |

OTHER PUBLICATIONS

An, et al. 1989, *Plant Cell* 1:115–122.
Banik, et al. 1996, *Plant Molecular Biology*, 31:1163–1172.
Banik, et al. 1997, *Mol. Gen. Genet.* 253:599–608.
Benjavongkulchai, et al. 1986, *Planta,* 169:415–419.
Bevan, et al. 1983, *Nucl. Acids Res.* 12:369–385.
Blum, et al. 1987, *Electrophoresis,* 8:93–99.
Boersma, et al. 1992, *Res. Immunol.,* 143:503–512.
Boersma, et al. 1993 *Use of Synthetic Peptide Determinants for the Production of Antibodies* In: Immunohistochemistry II (A.C. Cuello, ed.) Wiley and Sons, Toronto, pp. 1–78.
Christensen, et al. 1992, *Plant Mol. Biol.* 18: 675–689.
Christou, et al. 1987, *Proc. Natl. Acad.Sci. USA* 84:3962.
Coruzzi, et al., 1984, *EMBO, J.* 3:1671–1679.
De Block, et al., 1987, *EMBO J.* 6:2513–2518.
Deshayes et al. 1985, *EMBO J* 4:2731–2737.
D'Halluin, et al. 1992, *Plant Cell* 4:1495–1505.
Draper, et al. 1982, *Plant Cell Physiol.* 23:451–458.
Entwistle 1988, *Carlsburg Res. Commun.* 53:247–258.
Gerlach, et al. 1979, *Nucleic Acids Res.,* 7:1869:1885.
Gruber, et al., 1993, "Vectors for Plant Transformation" In: *Methods in Plant Molecular Biology and Biotechnology,* Glick and Thompson, eds., CRC Press, Inc., Boca Raton, pp. 89–119.
Hain, et al. 1985, *Mol. Gen. Genet.* 199:161–168.
Hammond, et al. *Biotechnology and Genetic Engineering Reviews,* Dec. 1993, 11:147–169, "Progress in the Development of New Barley, Hop and Yeast Variants for Malting and Brewing".
Hensgens, et al. 1989, *Rice Genetics Newsletter,* 6:163–168.
Hiei, et al. 1994, *The Plant Journal* 6:271–282.
Horsch, et al. 1985, *Science* 227:1229–1231.
Horton, et al. 1989, *Gene* 77:61–68.
Ishida, et al. 1996, *Nature Biotechnology,* 14:745–750.
Jacobsen, et al. 1985, *Planta,* 163:430–437.
Janssen, et al. 1986, *Chromatographia,* 22:345–350.
Juge, et al. 1993, *Gene,* 130:159–166.
Kado 1991, *Crit. Rev. Plant Sci.* 10:1–32.
Keil, et al. 1986, *Nucl. Acids. Res.* 14:5641–5650.
Klein, et al. 1992, *Biotechnology* 10:286–291.
Laemmli 1970, *Nature,* 227:680–695.
Laursen et al. 1994, *Plant Mol. Biol.,* 24:51–61.
Leah, et al. 1991, *Journal Biological Chemistry* 266:1564–1573.
Lee, et al. 1989, *Plant Molecular Biology,* 13:21–29.
McCleary, et al. 1987, "Measurement of Cereal α–amylase: A New Assay Procedure", *J. Cereal Sciences* 6:237–251.
Mett, et al. 1993, *Proc. Natl.Acad.Sci.* 90:4567–4571.
Miki, et al. 1993 "Procedure for Introducing Foreign DNA into Plants", In: *Methods in Plant Molecular Biology and Biotechnology,* Glick and Thompson, eds., CRC Press, Inc., Boca Raton, pp. 67–88.
Mikkonen, et al. 1996, *Plant Mol. Biol.* 31:239–253.
Moloney, et al. 1989, *Plant Cell Reports* 8:238–242.
Rogers 1985, *J. Biol. Chem.,* 260:3731–3738.
Rogers, et al. 1983, *J. Biol. Chem.* 258:8169–8174.
Sambrook, et al. 1989, *Molecular Cloning: A Laboratory Manual,* section 7.40 (4 pgs.).
Sanford, et al. 1987, *Part. Sci. Technol.* 5:27–37.
Sanford 1988, *Tibtech,* 6:299–302.
Sanford 1990, *Physiol. Plant* 79:206–209.
Schwarz, et al. 1995, *Soc. Brewing Chemists,* 53:157–159, "Arabinoxylan Content of Commerical Beers".
Slade, et al. 1989, *Eur. J. Biochem.,* 185:533–539.
Sørensen, et al. 1996 *Mol. Gen. Genet.* 250:750–760.
Towbin, et al. 1979, *Proc. Natl. Acad. Sci. USA* 76:4350–4354.
Wan, et al. 1994, *Plant Physiol.* 104:37–48.
Wolf 1991, *Plant Physiol.* 96:1382–1384.
Yoder et al. 1994, *Bio/Technology* 12:263–267.
Zacharius, et al. 1969, *Anal. Biochem.,* 30:148–152.
Zhang, et al. 1991, *Bio/Technology* 9:996 (2 pgs.).
Zegers, et al. 1991, *Biochem. Biophys. Acta.* 1073:23–32.
Soor, et al. 1990, Anal. Biochem. 188:187–191.

*Primary Examiner*—David T. Fox
*Assistant Examiner*—Ashwin Mehta
*Attorney, Agent, or Firm*—Merchant & Gould P.C.

[57] ABSTRACT

A genomic nucleic acid sequence encoding a 62 kDa barley endoxylanase has been isolated and characterized. The genomic DNA sequences are used to transform plant cells for expression of enhanced amounts of active endoxylanase.

38 Claims, 17 Drawing Sheets

Development of endoxylanase (■) and α-amylase (□) activity in Triumph kernels 0 1 2 3 4 5 6 7 8 9 10 11 12 13 14 X ← 43 kD 0 1 2 3 4 5 6 7 8 9 10 11 12 13 14

Days after steep-in

Fig. 9A

```
              11         21         31         41         51         61
     GGCGACGAGGAGGAAGGCCTGCGCCTGCCGATCCCGGTAGACACCCTGAAGCCTCGTCTC
       G   D   E   E   G   L   R   L   P   I   P   V   D   T   L   K   P   R   L 71         81         91        101        111        121
     ACTTACCGCGTGGCCGGGTGGATCAGCCTGGGAGCAGCACGGGGCACCAGCCACCCCGTG
       T   Y   R   V   A   G   W   I   S   L   G   A   A   R   G   T   S   H   P   V 131        141        151        161        171        181
     CGCATCGACCTTGGCGTGGAAGACAATGGCAACGAGACCCTGGTGGAGTGCGGCGCGGTG
       R   I   D   L   G   V   E   D   N   G   N   E   T   L   V   E   C   G   A   V 191        201        211        221        231        241
     TGCGCCAAGGAGGGCGGGTGGTCGGAGATCATGGGCGCCTTCCGGCTCAGGACGGAGCCG
       C   A   K   E   G   G   W   S   E   I   M   G   A   F   R   L   R   T   E   P 251        261        271        281        291        301
     CGCAGCGCCGCGGTTTACGTCCACGGTGCCCCCGCCGGCGTCGACGTCAAGGTCATGGAT
       R   S   A   A   V   Y   V   H   G   A   P   A   G   V   D   V   K   V   M   D 311        321        331        341        351        361
     CTCCGCGTCTACCCGGTGGACCACAAGGCGCGCTTCAGGCAGCTCAAGGACAAGACTGAC
       L   R   V   Y   P   V   D   H   K   A   R   F   R   Q   L   K   D   K   T   D 371        381        391        401        411        421
     AAGGCGCGCAAGAGGGACGTGATTCTCAAGCTGGGCACGCCGGCGGGAGCGGGAGCGGGC
       K   A   R   K   R   D   V   I   L   K   L   G   T   P   A   G   A   G   A   G 431        441        451        461        471        481
     GCGGCGGCGTCCGTGCGCGTGGTGCAGTTGGACAACGCCTTCCCCTTCGGGACATGCATC
       A   A   A   S   V   R   V   V   Q   L   D   N   A   F   P   F   G   T   C   I 491        501        511        521        531        541
     AACACGTCCGTCATCCAGAAGCCGGCCTTCCTCGACTTCTTCACCAACCACTTCGACTGG
       N   T   S   V   I   Q   K   P   A   F   L   D   F   F   T   N   H   F   D   W 551        561        571        581        591        601
     GCCGTCTTCGAGAACGAGCTCAAGTGGTACCACACGGAGGTGCAGCAGGGCCAGCTCAAC
       A   V   F   E   N   E   L   K   W   Y   H   T   E   V   Q   Q   G   Q   L   N 611        621        631        641        651        661
     TACGCCGACGCCGACGCGCTGCTCGCGTTCTGCGACCGCCTGGGCAAGACCGTCCGCGGC
       Y   A   D   A   D   A   L   L   A   F   C   D   R   L   G   K   T   V   R   G 671        681        691        701        711        721
     CACTGCGTCTTCTGGTCCGTGGACGGCGACGTGCAGCAGTGGGTCAAGAACCTCAACAAG
       H   C   V   F   W   S   V   D   G   D   V   Q   Q   W   V   K   N   L   N   K
```

Fig. 9B

```
         731       741       751       761       771       781
GACCAGCTCAGGTCCGCCATGCAGAGCCGCCTCGAGGGCCTCGTCTCCCGCTACGCCGGC
 D   Q   L   R   S   A   M   Q   S   R   L   E   G   L   V   S   R   Y   A   G 791       801       811       821       831       841
AGGTTCAAGCACTACGACGTCAACAACGAGATGCTGCACGGCCGCTTCTTCCGGGACCGC
 R   F   K   H   Y   D   V   N   N   E   M   L   H   G   R   F   F   R   D   R 851       861       871       881       891       901
CTCGGCGACGAGGACGTCCCGGCGTACATGTTCAAGGAGGTGGCGCGGCTGGACCCGGAG
 L   G   D   E   D   V   P   A   Y   M   F   K   E   V   A   R   L   D   P   E 911       921       931       941       951       961
CCCGTGCTCTTCGTCAACGACTACAACGTGGAGTGCGGCAACGACCCCAACGCGACGCCG
 P   V   L   F   V   N   D   Y   N   V   E   C   G   N   D   P   N   A   T   P 971       981       991      1001      1011      1021
GAGAAGTACGCCGAGCAGGTCGCATGGCTGCAGAGCTGCGGCGCGGTGGTGCGCGGCATC
 E   K   Y   A   E   Q   V   A   W   L   Q   S   C   G   A   V   V   R   G   I 1031      1041      1051      1061      1071      1081
GGGCTGCAGGGCCACGTGCAAAACCCGGTCGGGGAGGTCATCTGCGCCGCGCTCGACAGG
 G   L   Q   G   H   V   Q   N   P   V   G   E   V   I   C   A   A   L   D   R 1091      1101      1111      1121      1131      1141
CTCGCCAAGACGGGGGTGCCCATCTGGTTCACCGAGCTCGACGTGCCGGAGTACGACGTG
 L   A   K   T   G   V   P   I   W   F   T   E   L   D   V   P   E   Y   D   V 1151      1161      1171      1181      1191      1201
GGCCTCCGCGCCAAGGACCTGGAGGTGGTGCTCCGGGAGGCGTACGCGCACCCGGCCGTG
 G   L   R   A   K   D   L   E   V   V   L   R   E   A   Y   A   H   P   A   V 1211      1221      1231      1241      1251      1261
GAGGGCATCGTGTTCTGGGGCTTCATGCAGGGCACAATGTGGCGCCAGAACGCTTGGCTC
 E   G   I   V   F   W   G   F   M   Q   G   T   M   W   R   Q   N   A   W   L 1271      1281      1291      1301      1311      1321
GTCGACGCCGATGGCACCGTCAACGAGGCGGGCCAGATGTTCCTGAATCTGCAGAAGGAG
 V   D   A   D   G   T   V   N   E   A   G   Q   M   F   L   N   L   Q   K   E 1331      1341      1351      1361      1371      1381
TGGAAGACGGACGCGCGGGGGAACTTCGACGGCGACGGGAACTTCAAGTTCAGGGGCTTC
 W   K   T   D   A   R   G   N   F   D   G   D   G   N   F   K   F   R   G   F 1391      1401      1411      1421      1431      1441
TACGGCAGATACGTCGTGGAGGTTACGACGGCGAAGCGGAAGCAGATGCTCAATACCTCC
 Y   G   R   Y   V   V   E   V   T   T   A   K   R   K   Q   M   L   N   T   S
```

Fig. 9C

```
       1451        1461        1471        1481        1491        1501
ACGGTGGAGAAAGGGGACAACACACCTGTCGTCGTGGATTTGGCTGACGCCTGAcggtga
  T   V   E   K   G   D   N   T   P   V   V   V   D   L   A   D   A 1511        1521        1531        1541        1551        1561
atctatctaagaaactatttatttatacctatctaattacatgcaacacgtcaagggata 1571        1581        1591        1601        1611        1621
attggttgtataattttcacatttctaaggtaacgggtattgtatttgtaagagaagtg 1631        1641        1651        1661        1671        1681
tatggtgtttgtactcctaaatctgatgaacatgattgaagcaaaatgcctattggtctt 1691
aacaaaaaaa
```

Fig. 12A

```
                                                            |--Sense Primer---|
taaatacggt ggccaccgtg atccatcatc cctcactact cacacagcag agatcatcaa   1805
tccgacgaac atcttcgcaa cctccaggcc agtctgctct cactagctag tcactctccc   1865

▮62 kDa Pre Pro Protein →
actcgcgtaa g▮ATG GCA AGC ACA ACT CAG gtatgtaact tgcatgcagc tagc     1918
             ▮Met Ala Ser Thr Thr Gln |------------------------
                                  5 acaccatgag tccagctata gctcatttgc atggtgcact tgtgtgctgc ttgtttcag   1977
---------------------------------Intron 1-----------------------|

GAC GTG AAC ATG GAC GGC AAC CTC GCC GGC TGC GTA CCG TTC GGC ACG    2025
Asp Val Asn Met Asp Gly Asn Leu Ala Gly Cys Val Pro Phe Gly Thr
            10              15                  20

GGC ACG ACG ACG CTC TCC GTG CAC ATC GAG GAA GAG ATG GCC ATG CTT    2073
Gly Thr Thr Thr Leu Ser Val His Ile Glu Glu Glu Met Ala Met Leu
        25                  30                  35

CCC GTC ACT GTG GCC GTG GGT GGC AAC AAG CCC AGC GGC CGG TAC GTC    2121
Pro Val Thr Val Ala Val Gly Gly Asn Lys Pro Ser Gly Arg Tyr Val
    40                  45                  50
        ▮pS400 →
CTC GTG GCT▮GGC CGC GCC GAC GAG GAG GAC GGC CTG CGC CTG CCG ATC    2169
Leu Val Ala▮Gly Arg Ala Asp Glu Glu Asp Gly Leu Arg Leu Pro Ile
55              60                  65                      70
                                |---Reverse Primer--|
CCG GTA GAC ACC CTG AAG CCT CGT CTC ACT TAC CGC GTG GCC GGG TGG    2217
Pro Val Asp Thr Leu Lys Pro Arg Leu Thr Tyr Arg Val Ala Gly Trp
            75                  80                  85

ATC AGC CTG GGA GCA GCA CGG GGC ACC AGC CAC CCC GTG CGC ATC GAC    2265
Ile Ser Leu Gly Ala Ala Arg Gly Thr Ser His Pro Val Arg Ile Asp
                90                  95                  100

CTT GGC GTG GAA GAC AAT GGC AAC GAG ACC CTG GTG GAG TGC GGC GCG    2313
Leu Gly Val Glu Asp Asn Gly Asn Glu Thr Leu Val Glu Cys Gly Ala
            105                 110                 115
                                                ▮[Putative Signal
GTG TGC GCC AAG GAG GGC GGG TGG TCG GAG ATC ▮ATG GGC GCC TTC CGG   2361
Val Cys Ala Lys Glu Gly Gly Trp Ser Glu Ile ▮Met Gly Ala Phe Arg
        120                 125              ▮130
Peptide] →
CTC AGG ACG GAG CCG CGC AGC GCC GCG GTT TAC GTC CAC GGC GCC CCC    2409
Leu Arg Thr Glu Pro Arg Ser Ala Ala Val Tyr Val His Gly Ala Pro
135                 140                 145                 150
```

Fig. 12B

```
                                     ■41kDa Intermediate →
GCC GGC GTC GAC GTC AAG GTC ATG GAT CTC CGC■GTC TAC CCG GTG GAC    2457
Ala Gly Val Asp Val Lys Val Met Asp Leu Arg Val Tyr Pro Val Asp
                155                 160                 165

CAC AAG GCG CGC TTC AGG CAG CTC AAG GAC AAG ACT GAC AAG gtgagagag  2508
His Lys Ala Arg Phe Arg Gln Leu Lys Asp Lys Thr Asp Lys |--------
            170                 175                 180 catgcatcca cgtaataacc acctgcatgc acactcgctt gatgtggcac gtaacgtgat  2568
--------------------------Intron 2------------------------------- catacgagct ccattgatgc ag GCG CGC AAG AGG GAC GTG ATT CTC AAG CTG   2620
----------------------|  Ala Arg Lys Arg Asp Val Ile Leu Lys Leu
                                    185                 190

GGC ACG CCG GCG GGA GCG GGA GCG GGC GCG GCG GCG TCC GTG CGC GTG   2668
Gly Thr Pro Ala Gly Ala Gly Ala Gly Ala Ala Ala Ser Val Arg Val
                195                 200                 205
     ■34 kDa Mature Protein →
GTG CAG■TTG GAC AAC GCC TTC CCC TTC GGG ACA TGC ATC AAC ACG TCC   2716
Val Gln Leu Asp Asn Ala Phe Pro Phe Gly Thr Cys Ile Asn Thr Ser
            210                 215                 220

GTC ATC CAG AAG CCG GCC TTC CTC GAC TTC TTC ACC AAC CAC TTG GAC   2764
Val Ile Gln Lys Pro Ala Phe Leu Asp Phe Phe Thr Asn His Leu Asp
        225                 230                 235

TGG GCC GTC TTC GAG AAC GAG CTC AAG TGG TAC CAC ACG GAG GTG CAG   2812
Trp Ala Val Phe Glu Asn Glu Leu Lys Trp Tyr His Thr Glu Val Gln
    240                 245                 250

CAG GGC CAG CTC AAC TAC GCC GAC GCC GAC GCG CTG CTC GCG TTC TGC   2860
Gln Gly Gln Leu Asn Tyr Ala Asp Ala Asp Ala Leu Leu Ala Phe Cys
255             260                 265                 270

GAC CGC CTG GGC AAG ACC GTC CGC GGC CAC TGC GTC TTC TGG TCC GTG   2908
Asp Arg Leu Gly Lys Thr Val Arg Gly His Cys Val Phe Trp Ser Val
                275                 280                 285

GAC GGC GAC GTG CAG CAG TGG GTT AAG AAC CTC AAC AAG GAC CAG CTC   2956
Asp Gly Asp Val Gln Gln Trp Val Lys Asn Leu Asn Lys Asp Gln Leu
                290                 295                 300

AGG TCC GCC ATG CAG AGC CGC CTC GAG GGC CTC GTC TCC CGC TAC GCC   3004
Arg Ser Ala Met Gln Ser Arg Leu Glu Gly Leu Val Ser Arg Tyr Ala
            305                 310                 315
```

Fig. 12C

```
GGC AGG TTC AAG CAC TAC GAC GTC AAC AAC GAG ATG CTG CAC GGC CGC    3052
Gly Arg Phe Lys His Tyr Asp Val Asn Asn Glu Met Leu His Gly Arg
    320                 325                 330

TTC TTC CGG GAC CGC CTC GGC GAC GAG GAC GTC CCG GCG TAC ATG TTC    3100
Phe Phe Arg Asp Arg Leu Gly Asp Glu Asp Val Pro Ala Tyr Met Phe
335                 340                 345                 350

AAG GAG GTG GCG CGG CTG GAC CCG GAG CCC GCG CTC TTC GTC AAC GAC    3148
Lys Glu Val Ala Arg Leu Asp Pro Glu Pro Ala Leu Phe Val Asn Asp
                355                 360                 365

TAC AAC GTG GAG TGC GGC AAC GAC CCC AAC GCG ACG CCG GAG AAG TAC    3196
Tyr Asn Val Glu Cys Gly Asn Asp Pro Asn Ala Thr Pro Glu Lys Tyr
        370                 375                 380

GCC GAG CAG GTC GCA TGG CTG CAG AGC TGC GGC GCG GTA GTG CGC GGC    3244
Ala Glu Gln Val Ala Trp Leu Gln Ser Cys Gly Ala Val Val Arg Gly
            385                 390                 395

ATC GGG CTG CAG GGC CAC GTG CAA AAC CCG GTC GGG GAG GTC ATC TGC    3292
Ile Gly Leu Gln Gly His Val Gln Asn Pro Val Gly Glu Val Ile Cys
        400                 405                 410

GCC GCG CTC GAC AGG CTC GCC AAG ACG GGC GTG CCC ATC TGG TTC ACC    3340
Ala Ala Leu Asp Arg Leu Ala Lys Thr Gly Val Pro Ile Trp Phe Thr
415                 420                 425                 430

GAG CTC GAC GTG CCG GAG TAC GAC GTG GGC CTC CGC GCC AAG GAC CTG    3388
Glu Leu Asp Val Pro Glu Tyr Asp Val Gly Leu Arg Ala Lys Asp Leu
                435                 440                 445

GAG GTG GTG CTC CGG GAG GCG TAC GCG CAC CCG GCG GTG GAG GGC ATC    3436
Glu Val Val Leu Arg Glu Ala Tyr Ala His Pro Ala Val Glu Gly Ile
            450                 455                 460

GTG TTC TGG GGC TTC ATG CAG GGA ACA ATG TGG CGC CAG AAC GCT TGG    3484
Val Phe Trp Gly Phe Met Gln Gly Thr Met Trp Arg Gln Asn Ala Trp
        465                 470                 475

CTC GTC GAC GCC GAC GGC ACC GTC AAC GAG GCG GGG CAG ATG TTC CTG    3532
Leu Val Asp Ala Asp Gly Thr Val Asn Glu Ala Gly Gln Met Phe Leu
        480                 485                 490

AAT CTG CAG AAG GAG TGG AAG ACG GAC GCG CGG GGG AAC TTC GAC GGC    3580
Asn Leu Gln Lys Glu Trp Lys Thr Asp Ala Arg Gly Asn Phe Asp Gly
495                 500                 505                 510
```

Fig. 12D

```
GAC GGG AAC TTC AAG TTC AGG GGC TTC TAC GGC AGA TAC GTC GTG GAG       3628
Asp Gly Asn Phe Lys Phe Arg Gly Phe Tyr Gly Arg Tyr Val Val Glu
                515             520                 525

GTT ACG ACG GCG AAG GGG AAG CAG ATC CTC AAG ACC TTC AGG GTG GAG       3676
Val Thr Thr Ala Lys Gly Lys Gln Ile Leu Lys Thr Phe Arg Val Glu
                530             535                 540
                                                        Stop
AAA GGG GAC AGC ACA CCT CTC GTC GTG GAT TTG GCC GAC GCC TGA cggtg     3726
Lys Gly Asp Ser Thr Pro Leu Val Val Asp Leu Ala Asp Ala
            545             550                 555 aatctatcta agaaactatt tatttatacc tatctaatta catgcaacac gtcaagtgat     3786
aattggttgt ataattttca catttctaag gtaacgggta ttgtattttg taagagaagt     3846
ctaaggtatt tgtactccta aatctgatga acatgattga agcaaaaggc ctattggtgt     3906
tgctagcaaa taa                                                        3919
```

FIG. 13
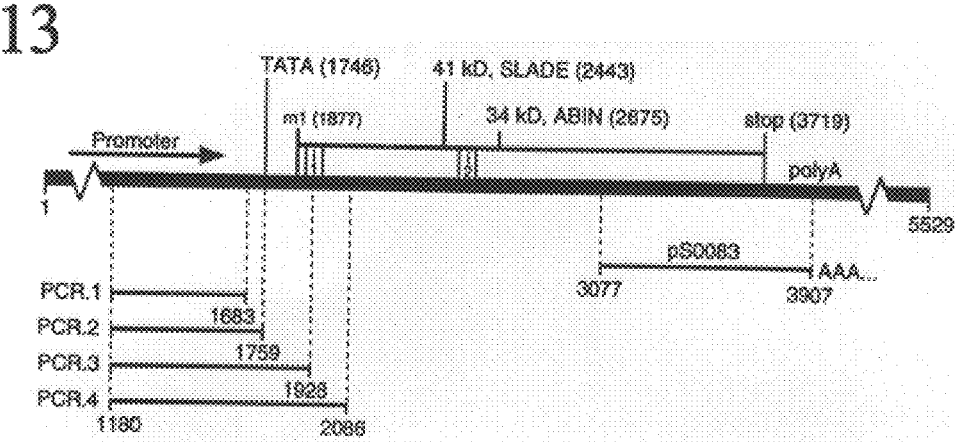
FIG. 14
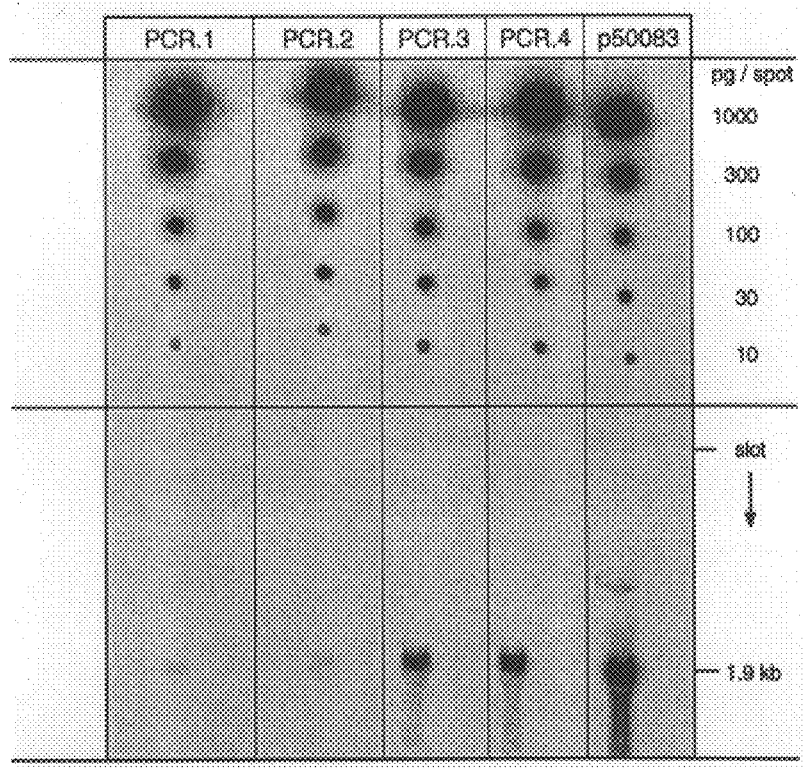
FIG. 15

SEQUENCE LISTING

<160> NUMBER OF SEQ ID NOS: 22

<210> SEQ ID NO 1
<211> LENGTH: 5529
<212> TYPE: DNA
<213> ORGANISM: barley

<400> SEQUENCE: 1

-continued

```
tctagagctc gcggccgcga gctctaatac gactcactat agggcgtcga ctcgatcaca      60
gtctcctaga aaatggcgtc gcaccttaaa ttttctgcaa tgagaatcgt cctggatacc     120
aatacctttc atatatttaa attcagagtg ggaagatctc cagaacaata tcagtcctag     180
atacacttga actattttgg attttaatgt tttgataata cttgaaatca cttttgtaa      240
acattaaatt gtataaaagt gaaaactaac acatatctcc attgagtcac ccaaattctc     300
aagatgttgt gcatacgttt taggcatatt ttaattatgt aacacacact aaattttaga    360
cacatattac aattattaca taaaaaggaa cgctattgta attgcgtaac tcaagtttag    420
aaaatacttt tccgtttcaa aatataagac cttttagaga ttttaatatg aactatatgc    480
gaatgtatat agacatattt tagcgtgtac attcattcat tttgttccgt atgtagtata    540
tattgaaatc tttaaaaggc ctgatattta ggaacggagg gagtactaca catgtaattt    600
aagcagatga tgtttatttc atatatattt cgactatttc ataattattt tgcaatacaa    660
aaatgataaa atggtgattt ataaatagtg aacaatgcat gcattgttta tctttccaaa    720
atcattattt cgtcatttcc aaaatcaaaa tttgcacgtg cgtaatatac atccatataa    780
acttattgat ttttgtaaga atattttgaa actcaaaaaa tactattttg tcacttcaaa    840
atatagtgct cactggaggt ctggagttct tccttcaagg tgagttttg attggacacc    900
ctcatattta gtgtcacact ttgactatga caatttacgg tgaggattct ctttcaaata   960
caaactcaat atttctcaaa aaatatttat gtagcatata aactacaatt catttttgta  1020
tagatgatca aggcttaacg caaaacacga gggctcctaa tgcacccgga aaaggaatt   1080
acacggattg ttatacccct ctcattgtta tatgccgtac gtagggtcat ttaaaatgta  1140
cagtcttctt catgcacggt gtgttgcttg cttgccccgc aacgaacgat tgcacgtact  1200
cctaaatctg atgaatctga tgaacatgtt tatgcgattg cttaacgtga ttagacagat  1260
cgagctactc tagtccctag gaggcaagag caagattcgg gaactatcgt ggtgtccatc  1320
catactggac gtgtggagcc gttttctgta acttgaagcc atgcattgca agggcacgct  1380
cgaatttagc atgcaggaat tagttacatc gtcgtcacca caagtgaggg cggctgcaag  1440
ttcatgcagg aattagtaac atcgccgtcg aggaattaaa tggtacgtgc gtgctctact  1500
accacgtctc gtttgggaaa tcgtagcact cgccaggaag gtctcagcct ttgtgtgttg  1560
tgcaatcttc actgttactc aagagcagca agcatgcgag agagagttcg ttgcttccgg  1620
tttgtgcctt gttcgttatt gctcttcacc gttactcttt ccatcctgtg ataacgactc  1680
gactatatcc atctcgaatt cccgatcgac tcaacgtcgc cagccgccgc caaatttcgc  1740
ccctttaaat acggtggcca ccgtgatcca tcatccctca ctactcacac agcagagatc  1800
atcaatccga cgaacatctt cgcaacctcc aggccagtct gctctcacta gctagtcact  1860
ctcccactcg cgtaagatgg caagcacaac tcaggtatgt aacttgcatg cagctagcac  1920
accatgagtc cagctatagc tcatttgcat ggtgcacttg tgtgctgctt gtttcaggac  1980
gtgaacatgg acggcaacct cgccggctgc gtaccgttcg gcacgggcac gacgacgctc  2040
tccgtgcaca tcgaggaaga gatggccatg cttcccgtca ctgtggccgt gggtggcaac  2100
aagcccagcg gccggtacgt cctcgtggct ggccgcgccg acgaggagga cggcctgcgc  2160
ctgccgatcc cggtagacac cctgaagcct cgtctcactt accgcgtggc cgggtggatc  2220
agcctgggag cagcacgggg caccagccac cccgtgcgca tcgacttggg cgtggaagac  2280
aatggcaacg agaccctggt ggagtgcggc gcggtgtgcg ccaaggaggg cggtggtcg   2340
gagatcatgg gcgccttccg gctcaggacg gagccgcgca gcgccgcggt ttacgtccac  2400
```

-continued

```
ggcgccccg   ccggcgtcga   cgtcaaggtc   atggatctcc   gcgtctaccc   ggtggaccac   2460
aaggcgcgct  tcaggcagct   caaggacaag   actgacaagg   tgagagagca   tgcatccacg   2520
taataaccac  ctgcatgcac   actcgcttga   tgtggcacgt   aacgtgatca   tacgagctcc   2580
attgatgcag  gcgcgcaaga   gggacgtgat   tctcaagctg   ggcacgccgg   cgggagcggg   2640
agcgggcgcg  gcggcgtccg   tgcgcgtggt   gcagttggac   aacgccttcc   ccttcgggac   2700
atgcatcaac  acgtccgtca   tccagaagcc   ggccttcctc   gacttcttca   ccaaccactt   2760
ggactgggcc  gtcttcgaga   acgagctcaa   gtggtaccac   acggaggtgc   agcagggcca   2820
gctcaactac  gccgacgccg   acgcgctgct   cgcgttctgc   gaccgcctgg   gcaagaccgt   2880
ccgcggccac  tgcgtcttct   ggtccgtgga   cggcgacgtg   cagcagtggg   ttaagaacct   2940
caacaaggac  cagctcaggt   ccgccatgca   gagccgcctc   gagggcctcg   tctcccgcta   3000
cgccggcagg  ttcaagcact   acgacgtcaa   caacgagatg   ctgcacggcc   gcttcttccg   3060
ggaccgcctc  ggcgacgagg   acgtcccggc   gtacatgttc   aaggaggtgg   cgcggctgga   3120
cccggagccc  gcgctcttcg   tcaacgacta   caacgtggag   tgcggcaacg   accccaacgc   3180
gacgccggag  aagtacgccg   agcaggtcgc   atggctgcag   agctgcggcg   cggtagtgcg   3240
cggcatcggg  ctgcagggcc   acgtgcaaaa   cccggtcggg   gaggtcatct   cgccgcgct   3300
cgacaggctc  gccaagacgg   gcgtgcccat   ctggttcacc   gagctcgacg   tgccggagta   3360
cgacgtgggc  ctccgcgcca   aggacctgga   ggtggtgctc   cgggaggcgt   acgcgcaccc   3420
ggcggtggag  ggcatcgtgt   tctggggctt   catgcaggga   acaatgtggc   gccagaacgc   3480
ttggctcgtc  gacgccgacg   gcaccgtcaa   cgaggcgggg   cagatgttcc   tgaatctgca   3540
gaaggagtgg  aagacggacg   cgcggggaa   cttcgacggc   gacgggaact   tcaagttcag   3600
gggcttctac  ggcagatacg   tcgtggaggt   tacgacggcg   aagggaagc   agatcctcaa   3660
gaccttcagg  gtggagaaag   gggacagcac   acctctcgtc   gtggatttgg   ccgacgcctg   3720
acggtgaatc  tatctaagaa   actatttatt   tataccatc   taattacatg   caacacgtca   3780
agtgataatt  ggttgtataa   ttttcacatt   tctaaggtaa   cgggtattgt   attttgtaag   3840
agaagtctaa  ggtatttgta   ctcctaaatc   tgatgaacat   gattgaagca   aaaggcctat   3900
tggtgttgct  agcaaataat   tatgactcaa   tatcgtgaca   tatgaacatc   ttctatttta   3960
acactgtggc  tcatcatgtt   gccatttatt   tttctttcca   ccctcgttga   tgatggtgtg   4020
atgttcacat  gatcataatg   cattcgacat   gataaatccc   aaggctatga   gcttttcact   4080
gcacgctaca  ctttccatta   tattgtgcaa   ggaattgttt   aaaacttttt   aaaaaatctc   4140
aacgaccacg  aactacttcc   aatgcctaga   catataaaga   ctttcaaaaa   actaatcaaa   4200
tcctagacat  agttcttttg   aatcggtgaa   cggttttcg    aaccgacaaa   cattgttttc   4260
aaattttgta  tttttcaaaa   aaaaatcatg   aacagtttga   aatgcatgat   cagttttcga   4320
attcatgaat  attttcttac   tcatcaacgt   ttttgaattg   atcaactttt   ttcaaacaaa   4380
ttctgaataa  attttaaaaa   catgtgtttt   ttaatttatg   tcaatatttt   ctaaaatttc   4440
atggccattt  gttttcagat   tccttaatac   attttgaata   cactatcatt   ttttcaaaag   4500
catgaacacg  gttttgtttc   ttgaccattt   tttccaaatc   acgaatattt   tttataattg   4560
gtgaacaata  ttgcaaaact   atcaacattt   tttaatccac   aaaaattatg   atttccttaa   4620
aatgttttga  attcacatac   actttatgat   ttctcgaaca   tcttttttgaa   acccacaac   4680
ttttgaaatt  ttaaaatcga   atttgtggaa   agaaggaaaa   gaaaacagaa   tgagaaaaga   4740
```

-continued

```
aaagacagaa aaattaaata gcgcagtcga gccttgcaca tgggccggtc cattaacgct    4800
tatgcgggga tgatttgctg aaggaaagga agagaaaaga gatggagact gggattcaat    4860
cctttgtctc aaaggtaata acgctagacg ctaaccactc cactacttgg gcgtttgtgc    4920
tttgcgtcag tattgttttt ataaaacaac gtaacacgac gcaactttgc aacaacggac    4980
gacagaagca ctttgtgctt tagtattagg gatagatttt atagaatata tacccatg     5040 atgtttatgg attttttttg tctaaaatga ccacctactc aaccaaattg ctaaaaaac    5100 cacttttgga taaaattgat agacaagacc cctgatcgtg gcggcaggtg caccggccga    5160
gatgtcgcac ctgctgccac ggacggaggc ggcaaccctg ttcacatgac tgtttatgcg    5220
agggactgtt tactaaagat gaacaatatt taaaaaaat caaaaaatag cagagaaatt    5280
aaaaaaaaac tgaattttt tggcaagaaa gatgatcgat tgttctagct gggtttgaaa    5340
tttcaatctt ttatgttttt tcttttata ttttttttc aaaaatactg tttattttgg     5400
gtgaacaata atgtcgctgc gtcggagtga acagtgctgc cgtctctagg cgtggcggca    5460
ggtgccacct gtcagctggc gcgcctgttt ccatggccga ggaggccttt tttgttaatt    5520
tcatctaga                                                            5529
```

<210> SEQ ID NO 2
<211> LENGTH: 556
<212> TYPE: PRT
<213> ORGANISM: barley

<400> SEQUENCE: 2

```
Met Ala Ser Thr Thr Gln Asp Val Asn Met Asp Gly Asn Leu Ala Gly
 1               5                  10                  15

Cys Val Pro Phe Gly Thr Gly Thr Thr Thr Leu Ser Val His Ile Glu
                20                  25                  30

Glu Glu Met Ala Met Leu Pro Val Thr Val Ala Val Gly Gly Asn Lys
         35                  40                  45

Pro Ser Gly Arg Tyr Val Leu Val Ala Gly Arg Ala Asp Glu Glu Asp
     50                  55                  60

Gly Leu Arg Leu Pro Ile Pro Val Asp Thr Leu Lys Pro Arg Leu Thr
 65                  70                  75                  80

Tyr Arg Val Ala Gly Trp Ile Ser Leu Gly Ala Ala Arg Gly Thr Ser
                 85                  90                  95

His Pro Val Arg Ile Asp Leu Gly Val Glu Asp Asn Gly Asn Glu Thr
                100                 105                 110

Leu Val Glu Cys Gly Ala Val Cys Ala Lys Glu Gly Gly Trp Ser Glu
            115                 120                 125

Ile Met Gly Ala Phe Arg Leu Arg Thr Glu Pro Arg Ser Ala Ala Val
        130                 135                 140

Tyr Val His Gly Ala Pro Ala Gly Val Asp Val Lys Val Met Asp Leu
145                 150                 155                 160

Arg Val Tyr Pro Val Asp His Lys Ala Arg Phe Arg Gln Leu Lys Asp
                165                 170                 175

Lys Thr Asp Lys Ala Arg Lys Arg Asp Val Ile Leu Lys Leu Gly Thr
            180                 185                 190

Pro Ala Gly Ala Gly Ala Gly Ala Ala Ser Val Arg Val Val Gln
        195                 200                 205

Leu Asp Asn Ala Phe Pro Phe Gly Thr Cys Ile Asn Thr Ser Val Ile
    210                 215                 220

Gln Lys Pro Ala Phe Leu Asp Phe Phe Thr Asn His Leu Asp Trp Ala
```

```
                    225                 230                 235                 240

Val Phe Glu Asn Glu Leu Lys Trp Tyr His Thr Glu Val Gln Gln Gly
                        245                 250                 255

Gln Leu Asn Tyr Ala Asp Ala Asp Ala Leu Leu Ala Phe Cys Asp Arg
                        260                 265                 270

Leu Gly Lys Thr Val Arg Gly His Cys Val Phe Trp Ser Val Asp Gly
                        275                 280                 285

Asp Val Gln Gln Trp Val Lys Asn Leu Asn Lys Asp Gln Leu Arg Ser
                        290                 295                 300

Ala Met Gln Ser Arg Leu Glu Gly Leu Val Ser Arg Tyr Ala Gly Arg
        305                 310                 315                 320

Phe Lys His Tyr Asp Val Asn Asn Glu Met Leu His Gly Arg Phe Phe
                        325                 330                 335

Arg Asp Arg Leu Gly Asp Glu Asp Val Pro Ala Tyr Met Phe Lys Glu
                        340                 345                 350

Val Ala Arg Leu Asp Pro Glu Pro Ala Leu Phe Val Asn Asp Tyr Asn
                        355                 360                 365

Val Glu Cys Gly Asn Asp Pro Asn Ala Thr Pro Glu Lys Tyr Ala Glu
                        370                 375                 380

Gln Val Ala Trp Leu Gln Ser Cys Gly Ala Val Val Arg Gly Ile Gly
        385                 390                 395                 400

Leu Gln Gly His Val Gln Asn Pro Val Gly Glu Val Ile Cys Ala Ala
                        405                 410                 415

Leu Asp Arg Leu Ala Lys Thr Gly Val Pro Ile Trp Phe Thr Glu Leu
                        420                 425                 430

Asp Val Pro Glu Tyr Asp Val Gly Leu Arg Ala Lys Asp Leu Glu Val
                        435                 440                 445

Val Leu Arg Glu Ala Tyr Ala His Pro Ala Val Glu Gly Ile Val Phe
        450                 455                 460

Trp Gly Phe Met Gln Gly Thr Met Trp Arg Gln Asn Ala Trp Leu Val
        465                 470                 475                 480

Asp Ala Asp Gly Thr Val Asn Glu Ala Gly Gln Met Phe Leu Asn Leu
                        485                 490                 495

Gln Lys Glu Trp Lys Thr Asp Ala Arg Gly Asn Phe Asp Gly Asp Gly
                        500                 505                 510

Asn Phe Lys Phe Arg Gly Phe Tyr Gly Arg Tyr Val Val Glu Val Thr
                        515                 520                 525

Thr Ala Lys Gly Lys Gln Ile Leu Lys Thr Phe Arg Val Glu Lys Gly
                        530                 535                 540

Asp Ser Thr Pro Leu Val Val Asp Leu Ala Asp Ala
        545                 550                 555

<210> SEQ ID NO 3
<211> LENGTH: 395
<212> TYPE: PRT
<213> ORGANISM: barley

<400> SEQUENCE: 3

Val Tyr Pro Val Asp His Lys Ala Arg Phe Arg Gln Leu Lys Asp Lys
        1               5                   10                  15

Thr Asp Lys Ala Arg Lys Arg Asp Val Ile Leu Lys Leu Gly Thr Pro
                        20                  25                  30

Ala Gly Ala Gly Ala Gly Ala Ala Ala Ser Val Arg Val Val Gln Leu
                        35                  40                  45
```

Asp Asn Ala Phe Pro Phe Gly Thr Cys Ile Asn Thr Ser Val Ile Gln
            50                   55                      60

Lys Pro Ala Phe Leu Asp Phe Phe Thr Asn His Leu Asp Trp Ala Val
 65                   70                      75                      80

Phe Glu Asn Glu Leu Lys Trp Tyr His Thr Glu Val Gln Gln Gly Gln
                    85                      90                      95

Leu Asn Tyr Ala Asp Ala Asp Ala Leu Leu Ala Phe Cys Asp Arg Leu
                100                 105                 110

Gly Lys Thr Val Arg Gly His Cys Val Phe Trp Ser Val Asp Gly Asp
                115                 120                 125

Val Gln Gln Trp Val Lys Asn Leu Asn Lys Asp Gln Leu Arg Ser Ala
        130                 135                 140

Met Gln Ser Arg Leu Glu Gly Leu Val Ser Arg Tyr Ala Gly Arg Phe
145                 150                 155                 160

Lys His Tyr Asp Val Asn Asn Glu Met Leu His Gly Arg Phe Phe Arg
                165                 170                 175

Asp Arg Leu Gly Asp Glu Asp Val Pro Ala Tyr Met Phe Lys Glu Val
                180                 185                 190

Ala Arg Leu Asp Pro Glu Pro Ala Leu Phe Val Asn Asp Tyr Asn Val
        195                 200                 205

Glu Cys Gly Asn Asp Pro Asn Ala Thr Pro Glu Lys Tyr Ala Glu Gln
        210                 215                 220

Val Ala Trp Leu Gln Ser Cys Gly Ala Val Arg Gly Ile Gly Leu
225                 230                 235                 240

Gln Gly His Val Gln Asn Pro Val Gly Glu Val Ile Cys Ala Ala Leu
                245                 250                 255

Asp Arg Leu Ala Lys Thr Gly Val Pro Ile Trp Phe Thr Glu Leu Asp
                260                 265                 270

Val Pro Glu Tyr Asp Val Gly Leu Arg Ala Lys Asp Leu Glu Val Val
                275                 280                 285

Leu Arg Glu Ala Tyr Ala His Pro Ala Val Glu Gly Ile Val Phe Trp
        290                 295                 300

Gly Phe Met Gln Gly Thr Met Trp Arg Gln Asn Ala Trp Leu Val Asp
305                 310                 315                 320

Ala Asp Gly Thr Val Asn Glu Ala Gly Gln Met Phe Leu Asn Leu Gln
                325                 330                 335

Lys Glu Trp Lys Thr Asp Ala Arg Gly Asn Phe Asp Gly Asp Gly Asn
                340                 345                 350

Phe Lys Phe Arg Gly Phe Tyr Gly Arg Tyr Val Val Glu Val Thr Thr
                355                 360                 365

Ala Lys Gly Lys Gln Ile Leu Lys Thr Phe Arg Val Glu Lys Gly Asp
        370                 375                 380

Ser Thr Pro Leu Val Val Asp Leu Ala Asp Ala
385                 390                 395

<210> SEQ ID NO 4
<211> LENGTH: 348
<212> TYPE: PRT
<213> ORGANISM: barley

<400> SEQUENCE: 4

Leu Asp Asn Ala Phe Pro Phe Gly Thr Cys Ile Asn Thr Ser Val Ile
  1               5                  10                  15

Gln Lys Pro Ala Phe Leu Asp Phe Phe Thr Asn His Leu Asp Trp Ala
                20                  25                  30

-continued

```
Val Phe Glu Asn Glu Leu Lys Trp Tyr His Thr Glu Val Gln Gln Gly
             35                  40                  45
Gln Leu Asn Tyr Ala Asp Ala Asp Ala Leu Leu Ala Phe Cys Asp Arg
         50                  55                  60
Leu Gly Lys Thr Val Arg Gly His Cys Val Phe Trp Ser Val Asp Gly
 65                  70                  75                  80
Asp Val Gln Gln Trp Val Lys Asn Leu Asn Lys Asp Gln Leu Arg Ser
                 85                  90                  95
Ala Met Gln Ser Arg Leu Glu Gly Leu Val Ser Arg Tyr Ala Gly Arg
            100                 105                 110
Phe Lys His Tyr Asp Val Asn Asn Glu Met Leu His Gly Arg Phe Phe
        115                 120                 125
Arg Asp Arg Leu Gly Asp Glu Asp Val Pro Ala Tyr Met Phe Lys Glu
    130                 135                 140
Val Ala Arg Leu Asp Pro Glu Pro Ala Leu Phe Val Asn Asp Tyr Asn
145                 150                 155                 160
Val Glu Cys Gly Asn Asp Pro Asn Ala Thr Pro Glu Lys Tyr Ala Glu
                165                 170                 175
Gln Val Ala Trp Leu Gln Ser Cys Gly Ala Val Val Arg Gly Ile Gly
            180                 185                 190
Leu Gln Gly His Val Gln Asn Pro Val Gly Glu Val Ile Cys Ala Ala
        195                 200                 205
Leu Asp Arg Leu Ala Lys Thr Gly Val Pro Ile Trp Phe Thr Glu Leu
    210                 215                 220
Asp Val Pro Glu Tyr Asp Val Gly Leu Arg Ala Lys Asp Leu Glu Val
225                 230                 235                 240
Val Leu Arg Glu Ala Tyr Ala His Pro Ala Val Glu Gly Ile Val Phe
                245                 250                 255
Trp Gly Phe Met Gln Gly Thr Met Trp Arg Gln Asn Ala Trp Leu Val
            260                 265                 270
Asp Ala Asp Gly Thr Val Asn Glu Ala Gly Gln Met Phe Leu Asn Leu
        275                 280                 285
Gln Lys Glu Trp Lys Thr Asp Ala Arg Gly Asn Phe Asp Gly Asp Gly
    290                 295                 300
Asn Phe Lys Phe Arg Gly Phe Tyr Gly Arg Tyr Val Val Glu Val Thr
305                 310                 315                 320
Thr Ala Lys Gly Lys Gln Ile Leu Lys Thr Phe Arg Val Glu Lys Gly
                325                 330                 335
Asp Ser Thr Pro Leu Val Val Asp Leu Ala Asp Ala
            340                 345

<210> SEQ ID NO 5
<211> LENGTH: 30
<212> TYPE: PRT
<213> ORGANISM: barley

<400> SEQUENCE: 5

Val Tyr Pro Val Asp His Lys Ala Arg Phe Arg Gln Leu Lys Asp Lys
  1               5                  10                  15
Thr Asp Lys Ala Arg Lys Arg Asp Val Ile Leu Lys Leu Gly
             20                  25                  30

<210> SEQ ID NO 6
<211> LENGTH: 867
<212> TYPE: DNA
```

<213> ORGANISM: barley

<400> SEQUENCE: 6

| | | | | | |
|---|---|---|---|---|---|
| ccgggaccgc | ctcggcgacg | aggacgtccc | ggcgtacatg | ttcaaggagg | tggcgcggct | 60 |
| ggacccggag | cccgtgctct | tcgtcaacga | ctacaacgtg | gagtgcggca | acgacccaa | 120 |
| cgcgacgccg | gagaagtacg | ccgagcaggt | cgcatggctg | cagagctgcg | gcgcggtggt | 180 |
| gcgcggcatc | gggctgcagg | gccacgtgca | aaacccggtc | ggggaggtca | tctgcgccgc | 240 |
| gctcgacagg | ctcgccaaga | cggggtgcc | catctggttc | accgagctcg | acgtgccgga | 300 |
| gtacgacgtg | ggcctccgcg | ccaaggacct | ggaggtggtg | ctccgggagg | cgtacgcgca | 360 |
| cccggccgtg | gagggcatcg | tgttctgggg | cttcatgcag | ggcacaatgt | ggcgccagaa | 420 |
| cgcttggctc | gtcgacgccg | atggcaccgt | caacgaggcg | ggccagatgt | tcctgaatct | 480 |
| gcagaaggag | tggaagacgg | acgcgcgggg | gaacttcgac | ggcgacggga | acttcaagtt | 540 |
| cagggcttc | tacggcagat | acgtcgtgga | ggttacgacg | gcgaagcgga | agcagatgct | 600 |
| caatacctcc | acggtggaga | aggggacaa | cacacctgtc | gtcgtggatt | tggctgacgc | 660 |
| ctgacggtga | atctatctaa | gaaactattt | atttatacct | atctaattac | atgcaacacg | 720 |
| tcaaggata | attggttgta | taattttcac | atttctaagg | taacgggtat | tgtattttgt | 780 |
| aagagaagtg | tatggtgttt | gtactcctaa | atctgatgaa | catgattgaa | gcaaaatgcc | 840 |
| tattggtctt | aaaaaaaaaa | aaaaagg | | | | 867 |

<210> SEQ ID NO 7
<211> LENGTH: 778
<212> TYPE: DNA
<213> ORGANISM: barley

<400> SEQUENCE: 7

| | | | | | |
|---|---|---|---|---|---|
| gagctcgtcg | agtggctcaa | ctggctcaag | gccgaccatc | ggctcgacgg | ctggcgcttc | 60 |
| gacttcgcca | agggctactc | cgcggacgtc | gccaagattt | acattgaccg | ctcggagccc | 120 |
| agcttcgccg | tggccgagat | atggacgtcg | ctcgcgtacg | gcggggacgg | caagcccaac | 180 |
| ctcaaccagg | accagcaccg | gcaggagctg | gtgaactggg | tggacaaggt | tggcggcaaa | 240 |
| gggcccgcta | ccacgttcga | cttcaccacc | aagggcatcc | tcaacgtggc | cgtggagggc | 300 |
| gagctgtggc | ggctgcgcgg | cacagacggt | aaggcgccag | gcatgatcgg | gtggtggccg | 360 |
| gccaaggcgg | tgacctttgt | ggacaaccac | gacaccggct | ccacgcagca | catgtggccc | 420 |
| ttcccttctg | acagggtcat | gcagggatat | gcctacatcc | tcacgcaccc | agggacgcca | 480 |
| tgcatcttct | acgatcattt | cttcgactgg | ggcctgaagg | aggagatcga | tcgcttggtg | 540 |
| tcagtcagga | cccggcacgg | gatacacaac | gagagcaagc | tgcaaatcat | agaggccgac | 600 |
| gccgaccttt | atctcgccga | gatcgacggc | aaggtcatcg | tcaagctcgg | gccaagatac | 660 |
| gatgtgggga | acctcattcc | gggaggcttc | aaggtggccg | cgcacggcaa | tgactatgcc | 720 |
| gtatggcaga | aaatatgagc | aaaattgcga | gagcagctct | acaaattagt | ccgagctc | 778 |

<210> SEQ ID NO 8
<211> LENGTH: 1690
<212> TYPE: DNA
<213> ORGANISM: barley

<400> SEQUENCE: 8

| | | | | | |
|---|---|---|---|---|---|
| ggcgacgagg | aggaaggcct | gcgcctgccg | atcccggtag | acaccctgaa | gcctcgtctc | 60 |
| acttaccgcg | tggccgggtg | gatcagcctg | ggagcagcac | ggggcaccag | ccaccccgtg | 120 |

```
cgcatcgacc ttggcgtgga agacaatggc aacgagaccc tggtggagtg cggcgcggtg    180
tgcgccaagg agggcgggtg gtcggagatc atgggcgcct ccggctcag  acggagccg     240 cgcagcgccg cggtttacgt ccacggtgcc cccgccggcg tcgacgtcaa ggtcatggat    300
ctccgcgtct acccggtgga ccacaaggcg cgcttcaggc agctcaagga caagactgac    360
aaggcgcgca agagggacgt gattctcaag ctgggcacgc cggcgggagc gggagcgggc    420
gcggcggcgt ccgtgcgcgt ggtgcagttg acaacgcct  tccccttcgg acatgcatc    480 aacacgtccg tcatccagaa gccggccttc ctcgacttct tcaccaacca cttcgactgg    540
gccgtcttcg agaacgagct caagtggtac cacacggagg tgcagcaggg ccagctcaac    600
tacgccgacg ccgacgcgct gctcgcgttc tgcgaccgcc tgggcaagac cgtccgcggc    660
cactgcgtct tctggtccgt ggacggcgac gtgcagcagt gggtcaagaa cctcaacaag    720
gaccagctca ggtccgccat gcagagccgc tcgagggc   tcgtctcccg ctacgccggc    780
aggttcaagc actacgacgt caacaacgag atgctgcacg ccgcttcttc cgggaccgc    840 ctcggcgacg aggacgtccc ggcgtacatg ttcaaggagg tggcgcggct ggacccggag    900
cccgtgctct tcgtcaacga ctacaacgtg gagtgcggca cgaccccaa  cgcgacgccg    960 gagaagtacg ccgagcaggt cgcatggctg cagagctgcg gcgcggtggt gcgcggcatc   1020
gggctgcagg gccacgtgca aaacccggtc ggggaggtca tctgcgccgc gctcgacagg   1080
ctcgccaaga cggggtgcc  catctggttc accgagctcg acgtgccgga gtacgacgtg   1140
ggcctccgcg ccaaggacct ggaggtggtg ctccgggagg cgtacgcgca cccggccgtg   1200
gagggcatcg tgttctgggg cttcatgcag ggcacaatgt ggcgccagaa cgcttggctc   1260
gtcgacgccg atggcaccgt caacgaggcg ggccagatgt tcctgaatct gcagaaggag   1320
tggaagacgg acgcgcgggg gaacttcgac ggcgacggga acttcaagtt cagggcttc   1380 tacggcagat acgtcgtgga ggttacgacg gcgaagcgga agcagatgct caatacctcc   1440
acggtggaga aggggacaa  cacacctgtc gtcgtggatt tggctgacgc ctgacggtga   1500
atctatctaa gaaactattt atttatacct atctaattac atgcaacacg tcaagggata   1560
attggttgta taatttttcac atttctaagg taacgggtat tgtatttttgt aagagaagtg   1620 tatggtgttt gtactcctaa atctgatgaa catgattgaa gcaaaatgcc tattggtctt   1680
aacaaaaaaa                                                          1690
```

<210> SEQ ID NO 9
<211> LENGTH: 497
<212> TYPE: PRT
<213> ORGANISM: barley

<400> SEQUENCE: 9

Gly Asp Glu Glu Glu Gly Leu Arg Leu Pro Ile Pro Val Asp Thr Leu
 1               5                  10                  15

Lys Pro Arg Leu Thr Tyr Arg Val Ala Gly Trp Ile Ser Leu Gly Ala
                20                  25                  30

Ala Arg Gly Thr Ser His Pro Val Arg Ile Asp Leu Gly Val Glu Asp
            35                  40                  45

Asn Gly Asn Glu Thr Leu Val Glu Cys Gly Ala Val Cys Ala Lys Glu
        50                  55                  60

Gly Gly Trp Ser Glu Ile Met Gly Ala Phe Arg Leu Arg Thr Glu Pro
    65                  70                  75                  80

Arg Ser Ala Ala Val Tyr Val His Gly Ala Pro Ala Gly Val Asp Val

-continued

```
                        85                     90                      95
Lys Val Met Asp Leu Arg Val Tyr Pro Val Asp His Lys Ala Arg Phe
                       100                    105                     110

Arg Gln Leu Lys Asp Lys Thr Asp Lys Ala Arg Lys Arg Asp Val Ile
                115                    120                    125

Leu Lys Leu Gly Thr Pro Ala Gly Ala Gly Ala Gly Ala Ala Ala Ser
130                    135                    140

Val Arg Val Val Gln Leu Asp Asn Ala Phe Pro Phe Gly Thr Cys Ile
145                    150                    155                    160

Asn Thr Ser Val Ile Gln Lys Pro Ala Phe Leu Asp Phe Phe Thr Asn
                165                    170                    175

His Phe Asp Trp Ala Val Phe Glu Asn Glu Leu Lys Trp Tyr His Thr
                180                    185                    190

Glu Val Gln Gln Gly Gln Leu Asn Tyr Ala Asp Ala Asp Ala Leu Leu
                195                    200                    205

Ala Phe Cys Asp Arg Leu Gly Lys Thr Val Arg Gly His Cys Val Phe
                210                    215                    220

Trp Ser Val Asp Gly Asp Val Gln Gln Trp Val Lys Asn Leu Asn Lys
225                    230                    235                    240

Asp Gln Leu Arg Ser Ala Met Gln Ser Arg Leu Glu Gly Leu Val Ser
                245                    250                    255

Arg Tyr Ala Gly Arg Phe Lys His Tyr Asp Val Asn Asn Glu Met Leu
                260                    265                    270

His Gly Arg Phe Phe Arg Asp Arg Leu Gly Asp Glu Asp Val Pro Ala
                275                    280                    285

Tyr Met Phe Lys Glu Val Ala Arg Leu Asp Pro Glu Pro Val Leu Phe
                290                    295                    300

Val Asn Asp Tyr Asn Val Glu Cys Gly Asn Asp Pro Asn Ala Thr Pro
305                    310                    315                    320

Glu Lys Tyr Ala Glu Gln Val Ala Trp Leu Gln Ser Cys Gly Ala Val
                325                    330                    335

Val Arg Gly Ile Gly Leu Gln Gly His Val Gln Asn Pro Val Gly Glu
                340                    345                    350

Val Ile Cys Ala Ala Leu Asp Arg Leu Ala Lys Thr Gly Val Pro Ile
                355                    360                    365

Trp Phe Thr Glu Leu Asp Val Pro Glu Tyr Asp Val Gly Leu Arg Ala
370                    375                    380

Lys Asp Leu Glu Val Val Leu Arg Glu Ala Tyr Ala His Pro Ala Val
385                    390                    395                    400

Glu Gly Ile Val Phe Trp Gly Phe Met Gln Gly Thr Met Trp Arg Gln
                405                    410                    415

Asn Ala Trp Leu Val Asp Ala Asp Gly Thr Val Asn Glu Ala Gly Gln
                420                    425                    430

Met Phe Leu Asn Leu Gln Lys Glu Trp Lys Thr Asp Ala Arg Gly Asn
                435                    440                    445

Phe Asp Gly Asp Gly Asn Phe Lys Phe Arg Gly Phe Tyr Gly Arg Tyr
                450                    455                    460

Val Val Glu Val Thr Thr Ala Lys Arg Lys Gln Met Leu Asn Thr Ser
465                    470                    475                    480

Thr Val Glu Lys Gly Asp Asn Thr Pro Val Val Asp Leu Ala Asp
                485                    490                    495

Ala
```

<210> SEQ ID NO 10
<211> LENGTH: 18
<212> TYPE: DNA
<213> ORGANISM: barley

<400> SEQUENCE: 10
acacagcaga gatcatca                                                    18

<210> SEQ ID NO 11
<211> LENGTH: 16
<212> TYPE: DNA
<213> ORGANISM: barley

<400> SEQUENCE: 11
gtctcactta ccgcgt                                                      16

<210> SEQ ID NO 12
<211> LENGTH: 503
<212> TYPE: DNA
<213> ORGANISM: barley

<400> SEQUENCE: 12
aacgaacgat tgcacgtact cctaaatctg atgaatctga tgaacatgtt tatgcgattg      60
cttaacgtga ttagacagat cgagctactc tagtccctag gaggcaagag caagattcgg     120
gaactatcgt ggtgtccatc catactggac gtgtggagcc gttttctgta acttgaagcc     180
atgcattgca agggcacgct cgaatttagc atgcaggaat tagttacatc gtcgtcacca     240
caagtgaggg cggctgcaag ttcatgcagg aattagtaac atcgccgtcg aggaattaaa     300
tggtacgtgc gtgctctact accacgtctc gtttgggaaa tcgtagcact cgccaggaag     360
gtctcagcct ttgtgtgttg tgcaatcttc actgttactc aagagcagca agcatgcgag     420
agagagttcg ttgcttccgg tttgtgcctc gttcgttatt gctcttcacc gttactcttt     480
ccatcctgtg ataacgactc gac                                             503

<210> SEQ ID NO 13
<211> LENGTH: 579
<212> TYPE: DNA
<213> ORGANISM: barley

<400> SEQUENCE: 13
aacgaacgat tgcacgtact cctaaatctg atgaatctga tgaacatgtt tatgcgattg      60
cttaacgtga ttagacagat cgagctactc tagtccctag gaggcaagag caagattcgg     120
gaactatcgt ggtgtccatc catactggac gtgtggagcc gttttctgta acttgaagcc     180
atgcattgca agggcacgct cgaatttagc atgcaggaat tagttacatc gtcgtcacca     240
caagtgaggg cggctgcaag ttcatgcagg aattagtaac atcgccgtcg aggaattaaa     300
tggtacgtgc gtgctctact accacgtctc gtttgggaaa tcgtagcact cgccaggaag     360
gtctcagcct ttgtgtgttg tgcaatcttc actgttactc aagagcagca agcatgcgag     420
agagagttcg ttgcttccgg tttgtgcctc gttcgttatt gctcttcacc gttactcttt     480
ccatcctgtg ataacgactc gactatatcc atctcgaatt cccgatcgac tcaacgtcgc     540
cagccgccgc caaatttcgc ccctttaaat acggtggcc                            579

<210> SEQ ID NO 14
<211> LENGTH: 748
<212> TYPE: DNA
<213> ORGANISM: barley

<400> SEQUENCE: 14

```
aacgaacgat tgcacgtact cctaaatctg atgaatctga tgaacatgtt tatgcgattg     60
cttaacgtga ttagacagat cgagctactc tagtccctag gaggcaagag caagattcgg    120
gaactatcgt ggtgtccatc catactggac gtgtggagcc gttttctgta acttgaagcc    180
atgcattgca agggcacgct cgaatttagc atgcaggaat tagttacatc gtcgtcacca    240
caagtgaggg cggctgcaag ttcatgcagg aattagtaac atcgccgtcg aggaattaaa    300
tggtacgtgc gtgctctact accacgtctc gtttgggaaa tcgtagcact cgccaggaag    360
gtctcagcct ttgtgtgttg tgcaatcttc actgttactc aagagcagca agcatgcgag    420
agagagttcg ttgcttccgg tttgtgcctc gttcgttatt gctcttcacc gttactcttt    480
ccatcctgtg ataacgactc gactatatcc atctcgaatt cccgatcgac tcaacgtcgc    540
cagccgccgc caaatttcgc cccttttaaat acggtggcca ccgtgatcca tcatccctca    600
ctactcacac agcagagatc atcaatccga cgaacatctt cgcaacctcc aggccagtct    660
gctctcacta gctagtcact ctcccactcg cgtaagatgg caagcacaac tcaggtatgt    720
aacttgcatg cagctagcac accatgag                                      748
```

<210> SEQ ID NO 15
<211> LENGTH: 1206
<212> TYPE: DNA
<213> ORGANISM: barley

<400> SEQUENCE: 15

```
aacgaacgat tgcacgtact cctaaatctg atgaatctga tgaacatgtt tatgcgattg     60
cttaacgtga ttagacagat cgagctactc tagtccctag gaggcaagag caagattcgg    120
gaactatcgt ggtgtccatc catactggac gtgtggagcc gttttctgta acttgaagcc    180
atgcattgca agggcacgct cgaatttagc atgcaggaat tagttacatc gtcgtcacca    240
caagtgaggg cggctgcaag ttcatgcagg aattagtaac atcgccgtcg aggaattaaa    300
tggtacgtgc gtgctctact accacgtctc gtttgggaaa tcgtagcact cgccaggaag    360
gtctcagcct ttgtgtgttg tgcaatcttc actgttactc aagagcagca agcatgcgag    420
agagagttcg ttgcttccgg tttgtgcctc gttcgttatt gctcttcacc gttactcttt    480
ccatcctgtg ataacgactc gactatatcc atctcgaatt cccgatcgac tcaacgtcgc    540
cagccgccgc caaatttcgc cccttttaaat acggtggcca ccgtgatcca tcatccctca    600
ctactcacac agcagagatc atcaatccga cgaacatctt cgcaacctcc aggccagtct    660
gctctcacta gctagtcact ctcccactcg cgtaagatgg caagcacaac tcaggtatgt    720
aacttgcatg cagctagcac accatgagtc cagctatagc tcatttgcat ggtgcacttg    780
tgtgctgctt gtttcaggac gtgaacatgg acggcaacct cgccggctgc gtaccgttcg    840
gcacgggcac gacgacgctc tccgtgcaca tcgaggaaga gatggccatg cttcccgtca    900
ctgtggccgt gggtggcaac aagcccagcg gccggtacgc cctcgtggct ggccgcgccg    960
acgaggagga cggcctgcgc ctgccgatcc cggtagacac cctgaagcct cgtctcactt   1020
accgcgtggc cgggtggatc agcctgggag cagcacgggg caccagccac cccgtgcgca   1080
tcgaccttgg cgtggaagac aatggcaacg agaccctggt ggagtgcggc gcggtgtgcg   1140
ccaaggaggg cgggtggtcg gagatcatgg gcgccttccg gctcaggacg gagccgcgca   1200
gcgccg                                                            1206
```

-continued

<210> SEQ ID NO 16
<211> LENGTH: 189
<212> TYPE: DNA
<213> ORGANISM: barley

<400> SEQUENCE: 16

| gtgctctact accacgtctc gtttgggaaa tcgtagcact cgccaggaag gtctcagcct | 60 |
| ttgtgtgttg tgcaatcttc actgttactc aagagcagca agcatgcgag agagagttcg | 120 |
| ttgcttccgg tttgtgcctc gttcgttatt gctcttcacc gttactcttt ccatcctgtg | 180 |
| ataacgact | 189 |

<210> SEQ ID NO 17
<211> LENGTH: 737
<212> TYPE: DNA
<213> ORGANISM: barley

<400> SEQUENCE: 17

| ctagaaactt tctgaatctg ctgtgtccag ttttatccgc ctcgagggac ccacctcatc | 60 |
| caggttattc aggaggtgtt gcttggaatt tgctgaccgg atttatgctt ctcaatcaga | 120 |
| aattcgcaag taactgcgaa agccatcttg agaaggtgcc atcagttgct gctgatctca | 180 |
| cgaactgttg cttacaagca ggacgtctga actgaacctt attttagtgc ggaaagctaa | 240 |
| accctttttgg ggttgatcat gtacaaaact ataccactcc cagttgagta gtttccgtgt | 300 |
| tcttgcaaat tcttcttggc ttgcctacag acatacagtt gcggtagatg aaggtttgta | 360 |
| attgtaacca cagcacacta ttcgatgaaa aatgctcgaa tgttctgtcc tcagaaaaac | 420 |
| agaggttgag gataactgac ggtcgtattg accggtgcct tcttatggaa ggcgaaggct | 480 |
| gcctccatct acatcacttg ggcattgaat cgccttttga gctcaccgta ccggccgata | 540 |
| acaaactccg gccgacatat ccactggccc aaaggagcat tcaagccgag cacacgagaa | 600 |
| agtgatttgc aagttgcaca ccggcagcaa ttccggcatg ctgcagcaca ctataaatac | 660 |
| ctggccagac acacaagctg aatgcatcag ttctccatcg tactcttcga gagcacagca | 720 |
| agagagagct gaagaac | 737 |

<210> SEQ ID NO 18
<211> LENGTH: 254
<212> TYPE: DNA
<213> ORGANISM: synthetic

<400> SEQUENCE: 18

| gatcgttcaa acatttggca ataaagtttc ttaagattga atcctgttgc cggtcttgcg | 60 |
| atgattatca tataatttct gttgaattac gttaagcatg taataattaa catgtaatgc | 120 |
| atgacgttat ttatgagatg ggttttttatg attagagtcc cgcaattata catttaatac | 180 |
| gcgatagaaa acaaaatata gcgcgcaaac taggataaat tatcgcgcgc ggtgtcatct | 240 |
| atgttactag atcg | 254 |

<210> SEQ ID NO 19
<211> LENGTH: 74
<212> TYPE: DNA
<213> ORGANISM: barley

<400> SEQUENCE: 19

| atggcgaaca aacacttgtc cctctcccctc ttcctcgtcc tccttggcct gtcggccagc | 60 |
| tggcctccgg gcaa | 74 |

<210> SEQ ID NO 20
<211> LENGTH: 1044
<212> TYPE: DNA
<213> ORGANISM: barley

<400> SEQUENCE: 20

```
ttggacaacg ccttcccctt cgggacatgc atcaacacgt ccgtcatcca gaagccggcc      60
ttcctcgact tcttcaccaa ccacttggac tgggccgtct tcgagaacga gctcaagtgg     120
taccacacgg aggtgcagca gggccagctc aactacgccg acgccgacgc gctgctcgcg     180
ttctgcgacc gcctgggcaa gaccgtccgc ggccactgcg tcttctggtc cgtggacggc     240
gacgtgcagc agtgggttaa gaacctcaac aaggaccagc tcaggtccgc catgcagagc     300
cgcctcgagg gcctcgtctc ccgctacgcc ggcaggttca agcactacga cgtcaacaac     360
gagatgctgc acgccgcttc ttccgggac cgcctcggcg acgaggacgt cccggcgtac     420
atgttcaagg aggtggcgcg gctggacccg gagcccgcgc tcttcgtcaa cgactacaac     480
gtggagtgcg gcaacgaccc caacgcgacg ccggagaagt acgccgagca ggtcgcatgg     540
ctgcagagct gcggcgcggt agtgcgcggc atcgggctgc agggccacgt gcaaaacccg     600
gtcggggagg tcatctgcgc gcgctcgac aggctcgcca agacgggcgt gcccatctgg     660
ttcaccgagc tcgacgtgcc ggagtacgac gtgggcctcc gcgccaagga cctggaggtg     720
gtgctccggg aggcgtacgc gcacccggcg gtggagggca tcgtgttctg gggcttcatg     780
cagggaacaa tgtggcgcca gaacgcttgg ctcgtcgacg ccgacggcac cgtcaacgag     840
gcggggcaga tgttcctgaa tctgcagaag gagtggaaga cggacgcgcg ggggaacttc     900
gacggcgacg ggaacttcaa gttcagggc ttctacggca gatacgtcgt ggaggttacg     960
acggcgaagg ggaagcagat cctcaagacc ttcagggtgg agaaagggga cagcacacct    1020
ctcgtcgtgg atttggccga cgcc                                          1044
```

<210> SEQ ID NO 21
<211> LENGTH: 1282
<212> TYPE: DNA
<213> ORGANISM: barley

<400> SEQUENCE: 21

```
ctccgcgtct acccggtgga ccacaaggcg cgcttcaggc agctcaagga caagactgac      60
aaggtgagag agcatgcatc cacgtaataa ccacctgcat gcacactcgc ttgatgtggc     120
acgtaacgtg atcatacgag ctccattgat gcaggcgcgc aagagggacg tgattctcaa     180
gctgggcacg ccggcgggag cgggagcggg cgcggcggcg tccgtgcgcg tggtgcagtt     240
ggacaacgcc ttcccttcg ggacatgcat caacacgtcc gtcatccaga agccggcctt     300
cctcgacttc ttcaccaacc acttggactg ggccgtcttc gagaacgagc tcaagtggta     360
ccacacggag gtgcagcagg gccagctcaa ctacgccgac gccgacgcgc tgctcgcgtt     420
ctgcgaccgc ctgggcaaga ccgtccgcgg ccactgcgtc ttctggtccg tggacggcga     480
cgtgcagcag tgggttaaga acctcaacaa ggaccagctc aggtccgcca tgcagagccg     540
cctcgagggc ctcgtctccc gctacgccgg caggttcaag cactacgacg tcaacaacga     600
gatgctgcac ggccgcttct ccgggaccg cctcggcgac gaggacgtcc ggcgtacat     660
gttcaaggag gtggcgcggc tggacccgga gcccgcgctc ttcgtcaacg actacaacgt     720
ggagtgcggc aacgaccca acgcgacgcc ggagaagtac gccgagcagg tcgcatggct     780
```

-continued

```
gcagagctgc ggcgcggtag tgcgcggcat cgggctgcag ggccacgtgc aaaacccggt      840
cggggaggtc atctgcgccg cgctcgacag gctcgccaag acgggcgtgc ccatctggtt      900
caccgagctc gacgtgccgg agtacgacgt gggcctccgc gccaaggacc tggaggtggt      960
gctccgggag gcgtacgcgc acccggcggt ggagggcatc gtgttctggg gcttcatgca     1020
gggaacaatg tggcgccaga acgcttggct cgtcgacgcc gacggcaccg tcaacgaggc     1080
ggggcagatg ttcctgaatc tgcagaagga gtggaagacg gacgcgcggg ggaacttcga     1140
cggcgacggg aacttcaagt tcaggggctt ctacggcaga tacgtcgtgg aggttacgac     1200
ggcgaagggg aagcagatcc tcaagacctt cagggtggag aaaggggaca gcacacctct     1260
cgtcgtggat ttggccgacg cc                                              1282
```

<210> SEQ ID NO 22
<211> LENGTH: 1372
<212> TYPE: DNA
<213> ORGANISM: barley

<400> SEQUENCE: 22

```
atgggcgcct tccggctcag gacggagccg cgcagcgccg cggtttacgt ccacggcgcc       60
cccgccggcg tcgacgtcaa ggtcatggat ctccgcgtct acccggtgga ccacaaggcg      120
cgcttcaggc agctcaagga caagactgac aaggtgagag agcatgcatc cacgtaataa      180
ccacctgcat gcacactcgc ttgatgtggc acgtaacgtg atcatacgag ctccattgat      240
gcaggcgcgc aagagggacg tgattctcaa gctgggcacg ccggcgggag cgggagcggg      300
cgcggcggcg tccgtgcgcg tggtgcagtt ggacaacgcc ttccccttcg ggacatgcat      360
caacacgtcc gtcatccaga agccggcctt cctcgacttc ttcaccaacc acttggactg      420
ggccgtcttc gagaacgagc tcaagtggta ccacacggag gtgcagcagg ccagctcaa      480 ctacgccgac gccgacgcgc tgctcgcgtt ctgcgaccgc ctgggcaaga ccgtccgcgg      540
ccactgcgtc ttctggtccg tggacggcga cgtgcagcag tgggttaaga acctcaacaa      600
ggaccagctc aggtccgcca tgcagagccg cctcgagggc ctcgtctccc gctacgccgg      660
caggttcaag cactacgacg tcaacaacga gatgctgcac ggccgcttct tccgggaccg      720
cctcggcgac gaggacgtcc cggcgtacat gttcaaggag gtggcgcggc tggacccgga      780
gcccgcgctc ttcgtcaacg actacaacgt ggagtgcggc aacgacccca acgcgacgcc      840
ggagaagtac gccgagcagg tcgcatggct gcagagctgc ggcgcggtag tgcgcggcat      900
cgggctgcag ggccacgtgc aaaacccggt cggggaggtc atctgcgccg cgctcgacag      960
gctcgccaag acgggcgtgc ccatctggtt caccgagctc gacgtgccgg agtacgacgt     1020
gggcctccgc gccaaggacc tggaggtggt gctccgggag gcgtacgcgc acccggcggt     1080
ggagggcatc gtgttctggg gcttcatgca gggaacaatg tggcgccaga acgcttggct     1140
cgtcgacgcc gacggcaccg tcaacgaggc ggggcagatg ttcctgaatc tgcagaagga     1200
gtggaagacg gacgcgcggg ggaacttcga cggcgacggg aacttcaagt tcaggggctt     1260
ctacggcaga tacgtcgtgg aggttacgac ggcgaagggg aagcagatcc tcaagacctt     1320
cagggtggag aaaggggaca gcacacctct cgtcgtggat ttggccgacg cc             1372
```

ARABINOXYLAN DEGRADATION

BACKGROUND OF THE INVENTION

1. Field of the Invention

This invention relates to a novel gene sequence encoding barley endoxylanase. More specifically, the invention relates to a genomic nucleic acid sequence and the 62 kDa endoxylanase it encodes, which is useful to express enhanced amounts of endoxylanase in host cells, and particularly in plants transformed with the gene, permitting enhanced degradation of cell wall xylan.

2. Background of the Invention

Degradation of cell wall arabinoxylans in germinating cereal grains is mediated by the action of endoxylanase. Cell wall degradation is of particular importance in fermentation processes that rely on fermentable sugars and nutrients provided by degradation of cereal grains. For example, barley malt, wheat malt, cereal grain malt, and cereal adjuncts, such as grain or grits, commonly maize or rice, are primary sources of required nutrients in the brewing process. When brewing beer, the amount of starch and protein degradation during malting and mashing, as well as the subsequent separation of spent grain from wort extract, greatly impacts the quality of the final product.

Oligo and polysaccharides, derived from P-glucans and arabinoxylans, that are not well degraded and that remain in the wort extract cause significant difficulties during brewing. Solubilized non-starch polysaccharides (nsp) are the primary cause of undesirable wort viscosity. Insoluble arabinoxylans absorb significant amounts of water and form a thick layer on the filter during wort filtration. Thus, both insoluble arabinoxylan and soluble arabinoxylan and β-glucan contribute to a reduced recovery of malt extract, impaired wort run-off during lautering (wort filtration), shortened half-life of wort filters, and haze formation in the beer product.

An analysis of the nsp content of fifteen commercial beers showed the arabinoxylan content ranged from 514 to 4211 μg/ml. Beers with the highest xylan (arabinoxylan) content were premium beers to which cereal adjunct had been added. In particular, beers made from wheat malt, known to contain 12.6% w/w xylan, contained a high amount of xylan. In the study, the viscosity of beer significantly correlated with xylan content, as well as β-glucan content, of the beer. (Schwarz and Han, 1995, "Arabinoxylan Content of Commercial Beers", *Soc. Brewing Chemists,* 53:157–159) It is therefore highly desirable to degrade arabinoxylan to short chain substituted arabinoxylo-oligomers early in the brewing process to avoid problems associated with non-degraded xylan.

Unlike β-glucans, which are largely degraded during malting and to a lesser extent in mashing, xylan degradation is limited during the brewing process. In large part, the limited degradation of xylan is due to the unavailability of endoxylanase early in malting. As discussed above, high levels of residual xylan in malt or wort results in viscosity, haze and filtration problems. Therefore, it is highly desirable to enhance degradation of xylan during cereal grain processing, particularly during the early stages of brewing, to reduce residual xylan in the wort and final product. One way to enhance the degradation of xylan is to increase the availability of endoxylanase, for example, by enhancing expression of the endoxylanase gene in the grain during industrial malting or by adding endoxylanase enzyme to the wort.

Endo-β-xylanase proteins previously purified from germinating barley include three 41 kDa isoforms of endoxylanase, XH1, XH2, and XH3, each with a pI of 5.2 (Slade, et al., 1989, *Eur. J. Biochem.* 185:533–539) and a 34 kDa endoxylanase with a pI of 4.6 (Benjavongkulchai, et al., 1986, *Planta* 169:415–419). A partial cDNA clone encoding the 41 kDa protein has been isolated (Banik, et al., 1996, *Plant Molecular Biology,* 31:1163–1172), however, the prior art does not indicate any protein has been expressed from this gene. As demonstrated in the Examples below, expression of this nucleic acid sequence resulted in little or no endoxylanase activity. (See Example 5 and FIGS. 18, 19 and 20.)

It would, therefore, be of great utility to isolate and characterize a gene encoding an active barley malt endoxylanase, and to express the endoxylanase gene in cereal grains during malting to bring about enhanced degradation of arabinoxylans in the malt and in the wort during mashing. Furthermore, expression of barley malt endoxylanase gene in an alternative host cell would provide quantities of purified enzyme for adding to the brewing process at the start of mashing to enhance degradation of arabinoxylan.

SUMMARY OF THE INVENTION

A genomic DNA sequence [Sequence ID No. 1] encoding a 62 kDa barley endoxylanase [Sequence ID No. 2] has been isolated and characterized. The genomic DNA coding sequence, when used to transform plant cells, is expressed as a 62 kDa preproprotein which is processed into a 41 kDa intermediate [Sequence ID No. 3] and then to an active 34 kDa protein [Sequence ID No. 4].

The present invention includes the genomic nucleic acid sequence of the barley endoxylanase gene, having a 5' untranslated region and two introns; the coding sequence of barley preproendoxylanase, including a signal peptide; the 62 kDa proprotein encoded by the genomic sequence, and nucleic acid constructs containing the genomic nucleic acid sequence or portions thereof. The invention further includes use of the genomic nucleic acid sequence, including all or part of the genomic sequence, to transform host cells and produce active endoxylanase, particularly plant cells, and more particularly to transform plants for enhanced expression of endoxylanase. The invention also includes use of an endoxylanase produced from the genomic DNA sequence to enhance arabinoxylan degradation, especially during brewing processes such as in beer production.

In a preferred embodiment of the invention, the sequence encoding all or a portion of the 62 kDa preproprotein is operatively linked to an early promoter such as the α-amylase promoter, and used to transform plant cells so that endoxylanase is expressed in the transformed plants during early stages of germination. Plants expressing endoxylanase early in germination are useful for brewing processes to reduce arabinoxylans.

The invention further includes use of an early promoter to produce degradative enzymes early in germination and/or in the commercial malting process. Plants transformed with gene constructs, including such enzymes operatively linked, e.g., driven by early promoters are useful in commercial brewing processes to provide a high quality malt, and a less viscous product.

BRIEF DESCRIPTION OF THE DRAWINGS

FIGS. 9(A–C) shows the nucleotide sequence and deduced amino acid sequence of a barley endoxylanase partial cDNA clone pS400. The published N-terminal amino acid sequence of the 42 kDa endoxylanases purified by Slade, et al. (1989) is shown in bold and the 34 kDa endoxylanase is in bold and underlined. The stop codon in the coding sequence is underlined.

FIGS. 12A–D shows the nucleotide sequence and deduced amino acid sequence of the transcribed region of the barley endoxylanase genomic clone xyl26. Coding sequence is shown in capital letters. The position of introns 1 and 2, indicated by a dotted line below the sequence, was deduced by alignment with the cDNA sequence of clone pS400 and an overlapping 340 nucleotide 5' cDNA clone amplified by RNA-PCR with the indicated sense and reverse primers. The relative position of the 5' end of the pS400 cDNA is indicated. The amino acid sequences given in bold and in bold with underlining, align with the determined N-terminal sequence of the purified 41 and 34 kDa endoxylanases, respectively, as indicated.

FIG. 13 is a schematic representation the barley endoxylanase xyl26 gene, located on a 5529 bp Xba1 fragment isolated from a genomic library. The location of PCR fragments (PCR.1–4) and the insert of cDNA clone pS0083 are shown. m1 indicates the first ATG codon downstream of the TATA box. The open box represents the open reading frame. Introns 1 and 2 are indicated by the boxes i1 and i2.

FIG. 14 shows a dot blot of the genomic clone xyl26 hybridized with 5 different endoxylanase oligonucleotide probes (PCR. 1–4 and pS0083).

FIG. 15 is a Northern blot of RNA, extracted from 5–7 day germinating barley kernels, hybridized with the probes defined in FIG. 14 to detect the 5' end of endoxylanase mRNA.

DETAILED DESCRIPTION OF THE INVENTION

Figure 1:
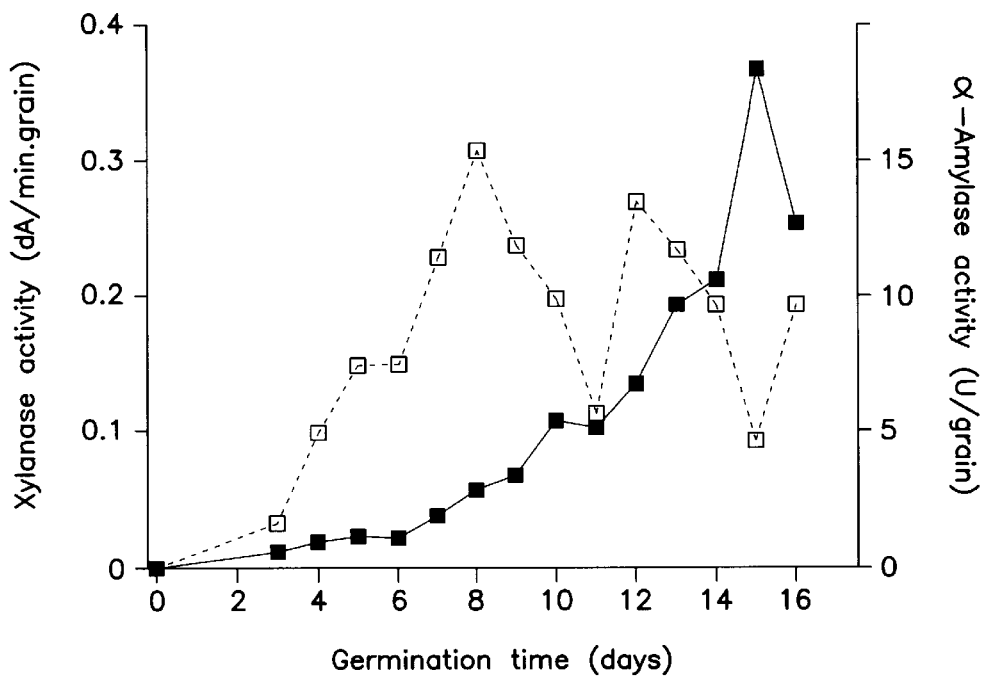
FIG. 1 is a graph showing the time course of α-amylase and endoxylanase enzyme activities during the process of germination in barley.

The present invention includes a genomic DNA sequence, its encoded amino acid sequence, transgenic cells and plants transformed with the genomic sequence and methods for degrading xylan using recombinant endoxylanase produced from the genomic DNA, particularly during brewing of beer. The invention also includes nucleic acid constructs expressing all or a portion of the genomic sequence, particularly those where expression is driven by an early promoter such as the α-amylase promoter.

Endoxylanase

Endoxylanase is a xylan-degrading enzyme produced by plants, for example, during germination of cereal grains. Endoxylanase is important in mediating degradation of linear and substituted xylan, a constituent of plant cell walls. Of particular importance is the degradation of xylan during commercial processes that use cereal grains, such as beer brewing. While plants, such as barley, naturally produce endoxylanase, the amount of enzyme and the timing of its production in the plant may be incompatible with desired processing. To improve commercial processing, it is therefore desirable to enhance cell wall degradation at a time conducive to the commercial process. For example, during beer production, it would be highly desirable to enhance endoxylanase production early in the malting process to more fully degrade cell wall linear and substituted xylan during malting and, subsequently, during mashing.

Endoxylanase Activity

As described more fully in the Examples below, endoxylanase activity has been detected in barley kernels during later stages of germination as compared to the activity of other hydrolytic enzymes, such as α-amylase. Similarly, expression of the gene encoding endoxylanase has been found to occur late in the germination process, as compared with the early expression of α-amylase genes. For the purposes of this invention, "late" activity refers to enzyme activity during the latter half of the germination period, when endogenous endoxylanase is active. "Early" activity refers to enzyme activity that is observed earlier in germination, e.g., during the first half of the germination period when α-amylase activity is detected. Under both micromalting and industrial malting conditions, expression of the endoxylanase gene in barley kernels cannot be detected, and significant levels of endoxylanase activity are not observed during malting, even after an extended period of time (e.g., 14 days). (See examples presented below and FIGS. 1 and 2.)

The late accumulation of endoxylanase activity during barley germination correlates with late transcription and translation of the gene encoding the enzyme. Similarly, the low endoxylanase activity present in barley malt is correlated with nondetectable levels of transcription and translation of the gene, as demonstrated by Northern blot and Western blot analyses. (See examples presented below and FIGS. 3–5). In one embodiment of the invention, endoxylanase activity is enhanced by increasing the amount of endoxylanase produced by a plant cell. In a preferred embodiment, endoxylanase activity is enhanced during brewing by inducing enhanced levels of endoxylanase production in barley at an early stage of germination and malting, for example, by transforming barley plants with a gene expressing active endoxylanase early in germination. Preferably, expression of endoxylanase is driven by an early promoter, such as the α-amylase promoter.

In an alternative embodiment, endoxylanase activity is enhanced during brewing by adding the enzyme directly in the brewing process. The enzyme is preferably produced by host cells transformed with a gene construct containing all or part of the genomic sequence of the invention.

Genomic Sequence Encoding a Barley Endoxylanase

The genomic nucleic acid sequence encoding a full length endoxylanase precursor was determined by methods described more fully in the Examples below. Briefly, using standard molecular biology techniques, a genomic clone, xyl26, cloned in Lambda Fix II vector (Stratagene Cat. No: 94610), was selected by screening plaque lifts of a barley genomic DNA library with a $^{32}$P-labeled 1691 bp insert of the barley endoxylanase cDNA clone pS400.

As shown in FIGS. 12A–D, the isolated genomic DNA fragment, xyl26[Sequence ID No. 1], includes a coding region encoding the endoxylanase precursor. Among other elements typically present in a gene, two introns and the full coding sequence for the 62 kDa protein are contained in the sequence. The coding region lies within an XbaI fragment of 5529 base pairs, subcloned from an 18 kilobase barley genomic clone (lambda). Coding sequence is shown in capital letters, beginning at position 1877 and ending at position 3721. Introns are underlined with a dotted line. Intron 1 is 83 bp long and spans nucleotides 1895 to 1977. Intron 2 is 91 bp long and spans nucleotides 2500 to 2590. The putative TATA box is located at position 1746 and the polyadenylation site is located at position 3914.

Active Recombinant Endoxylanase

The primary translation product of the endoxylanase genomic DNA sequence is a preproendoxylanase, which co-translationally enters the cellular secretion pathway. Following cleavage of the N-terminal signal peptide sequence, the first precursor form detected in barley is a proendoxylanase with an apparent molecular mass of 62 kDa. The mature form of the enzyme has a molecular mass of about 34 kDa [Sequence ID No. 4] and is produced from the precursor protein by proteolytic removal of N-terminal amino acids.

Figure 7:
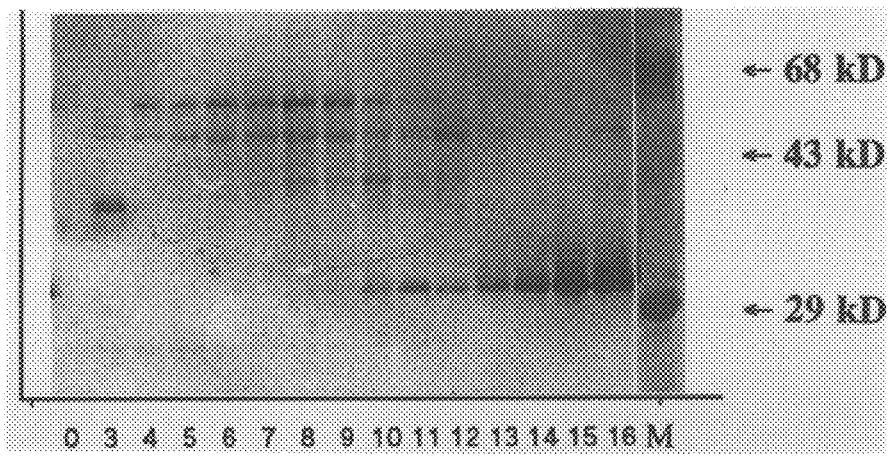
FIG. 7 is a Western blot used to detect endoxylanase in extracts of Triumph barley kernels sampled during germination and probed with anti-xylanase antiserum (Xyl-Bar-PC).
Figure 8:
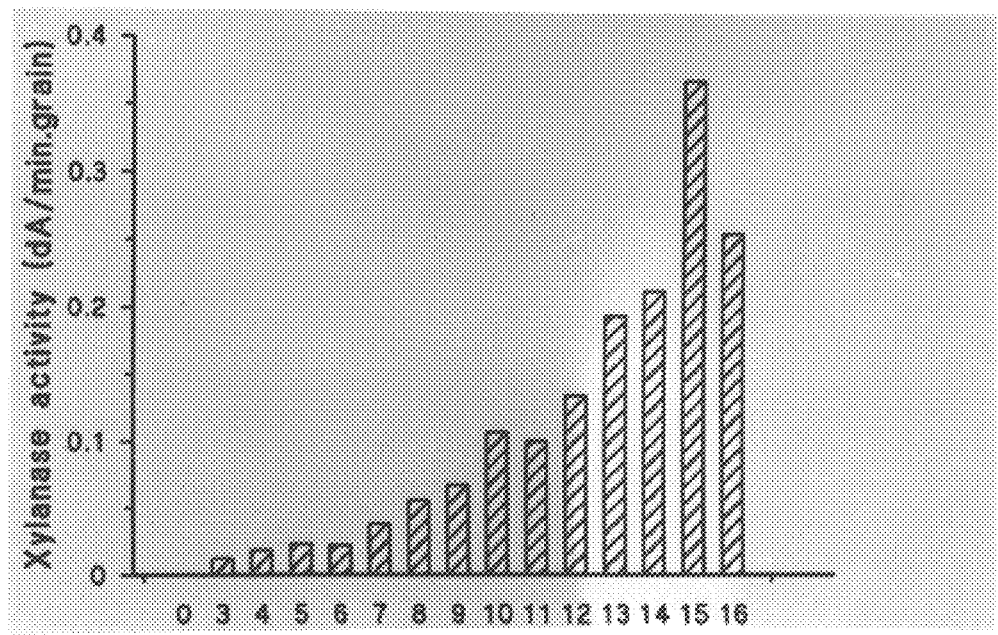
FIG. 8 is a graph showing the development of endoxylanase activity in Triumph barley kernels during germination.

Processing of the 62 kDa pro-endoxylanase to the 34 kDa form was demonstrated using Western blot assays of germinating barley kernel extracts. As described in the examples below and shown in FIG. 10, polyclonal antibodies (Xyl-Bar-PC) raised against the 34 kDa mature endoxylanase recognized a 62 kDa polypeptide in 6 day germinated kernels, while in 12 day germinated kernels a 34 kDa polypeptide, co-migrating with mature endoxylanase, was recognized. The 62 kDa polypeptide was identified as a precursor of the 34 kDa mature endoxylanase using Xyl"N"-Bar-PC polyclonal antibody. Xyl"N"-Bar-PC was raised against a deduced 30 residue peptide located upstream of the 34 kDa in the coding region (the first 30 residues of the 41 kDa polypeptide) [Sequence ID No. 5]. Since processing to the mature 34 kDa form removed the antibody epitope located to the N-terminus, only the 62 kDa pro-endoxylanase and larger precursor forms were recognized by this antibody. The sequential events of pro-endoxylanase synthesis and subsequent N-terminal processing was further confirmed by Western blot analysis of barley kernel extracts sampled during 16 days germination, using Xyl-Bar-PC antibodies, as described below and shown in FIG. 7. The 62 kDa pro-endoxylanase was first immunodetected after 4 days of germination, while the lower molecular mass forms were not detected until the following days. The mature 34 kDa endoxylanase was first clearly detectable after 10 days germination and increased in abundance over the following 6 days. A sharp increase in endoxylanase activity in these kernel extracts coincided with the appearance of the mature endoxylanase, as shown in FIG. 8.

Figure 11:
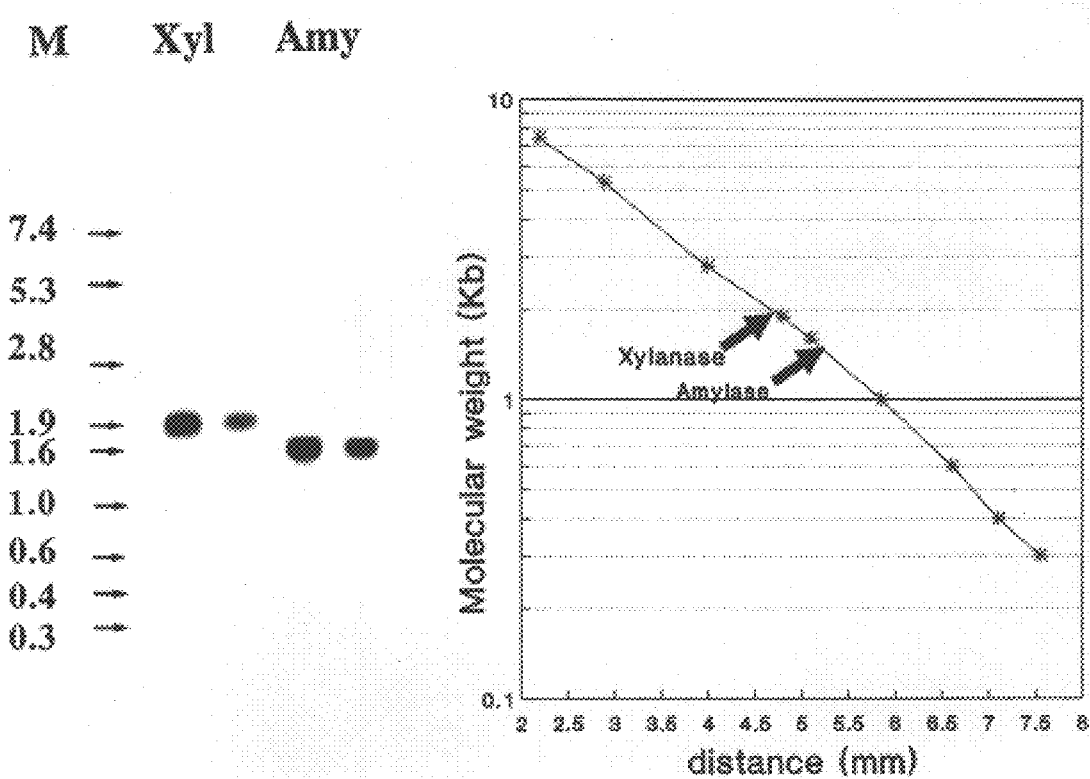
FIG. 11 is a Northern blot showing xylanase and α-amylase mRNA in extracts of germinated barley kernels (6 days) probed with the endoxylanase and α-amylase probes described above for FIG. 3. A semi-logarithmic plot estimating the size of the endoxylanase mRNA is also shown. "M" indicates RNA molecular mass markers. "xyl" indicates the endoxylanase mRNA. "amy" indicates α-amylase mRNA.

Based on Northern blot analysis, the barley endoxylanase gene (xyl26) produces an mRNA of about 1900 nucleotides as shown in FIG. 11. Using 5' specific PCR probes, as shown in FIGS. 13–15, the 5' end of the transcript was shown to lie upstream of the first methionine codon in the xyl26 coding region (position 1877). The xyl full-length cDNA, derived from overlapping RNA-PCR and pS400 cDNA clones, encodes a primary translation product of 61.4 kDa. Upon processing, a mature polypeptide of 34 kDa with N-terminal sequence identity to the 34 kDa barley endoxylanase is produced. A processing intermediate of 41 kDa [Sequence ID No. 3] has a predicted N-terminal sequence with identity to the 41 kDa endoxylanases purified by Slade, et al. 1989.

When a xyl26 gene expression construct encoding the 62 kDa precursor protein is used to transform plant cells, the recombinantly produced endoxylanase is enzymatically active. In contrast, as described in the Examples below and shown in FIGS. 18–20, plant cells transformed with cDNA fragments encoding truncated forms of the enzyme, e.g., either the 41 kDa intermediate or the 34 kDa mature endoxylanase protein, failed to produce active endoxylanase.

While not seeking to be bound by theory, it is possible that expression of the primary precursor form of the endoxylanase encoded by the xyl26 genomic clone is required for proper folding of the active protein. Alternatively, the precursor form may be necessary for intracellular transport of the protein. Many secreted enzymes are expressed in precursor form, using a signal peptide and propeptide for transit through the endoplasmic reticulum, intracellular targeting, folding or activation of the polypeptide. Because of its capacity to produce an active enzyme, the genomic nucleic acid sequence of the invention is particularly useful for producing transgenic plant cells and transgenic plants having enhanced endoxylanase activity.

Sequence Modifications

Applicants recognize, and include within the scope of their invention, a genomic DNA sequence for the 62 kDa barley endoxylanase which contains codons that are modified according to optimal codon frequencies for a particular cellular host.

Redundancy in the genetic code permits variation in the gene sequence shown in FIG. 12. In particular, specific codon preferences are recognized for a specific host such that the disclosed sequence can be adapted as preferred for the desired host. For example, rare codons having a frequency of less than about 20% in known sequences of the desired host are preferably replaced with higher frequency codons.

Additional sequence modifications are known to enhance protein expression in a cellular host. These include elimination of sequences encoding spurious polyadenylation signals, exon/intron splice site signals, transposon-like repeats, and other such well characterized sequences which may be deleterious to gene expression. The G-C content of the sequence may be adjusted to levels average for a given cellular host, as calculated by reference to known genes expressed in the host cell. Where possible, the sequence is modified to avoid predicted hairpin secondary mRNA structures. The genomic sequence might additionally be modified by the removal of the two introns.

Gene Delivery

The nucleic acid sequence encoding the preproendoxylanase may be delivered to plant cells for transient transfections or for incorporation into the plant's genome by known methods. Preferably, the gene is used to stably transform plant cells for expression of the protein in vivo.

To accomplish such delivery, the gene containing the coding sequence for the preproendoxylanase may be attached to regulatory elements needed for the expression of the gene in a particular host cell or system. These regulatory elements include, for example, promoters, terminators, and other elements that permit desired expression of the enzyme in a particular plant host, in a particular tissue or organ of a host such as aleurone, endosperm, or embryo tissues of the kernel, root, leaf, or flower, or in response to a particular signal.

Gene Constructs

The isolated genomic nucleic acid sequence of the invention can be incorporated into DNA constructs and used to transform or transfect a host cell. Many DNA vectors can be used, depending on the host cell and desired expression. Examples of suitable vectors include, but are not limited to, self-replicating or integration plasmids suitable for expression in prokaryotic or eukaryotic cells. FIGS. 17–20 describe the use of a pUC based plasmid for insertion of the isolated genomic sequence (e.g., pMC138) and its expression in transformed plant cells.

A typical DNA construct includes a promoter, the coding sequence of interest, and a terminator sequence coupled in operative association. Additional known regulatory elements can also be included in the construct.

Suitable constructs for the stable transformation of plant cells can include those having constitutive promoters such as the Ubi1 gene promoter (Christensen, et al., 1992, *Plant Mol. Biol.* 18: 675–689) driving expression of selectable markers such as the phosphinothricin acetyl transferase gene (bar) (De Block et al., 1987, *EMBO J.* 6: 2513–2518). Additionally, the plasmid can include other gene sequences such as resistance genes (required for the selection and amplification of host transformed cells), reporter genes or other elements. Examples of suitable plant transformation selection systems for cereals or other plants are described by Yoder and Goldsbrough, 1994, *Bio/Technology* 12: 263–267, and are incorporated herein by reference.

Promoters

A DNA construct of the invention includes a non-endoxylanase promoter sequence ("heterologous" promoter). As used herein, the term "heterologous", for the barley endoxylanse gene of the invention, is a nucleic acid sequence not normally found in the barley genome associated with the barley endoxylanase gene. For example, a heterologous sequence is one derived from a different cell type, different plant species, different organism, of one normally associated with a different gene. A heterologous promoter is one which does not drive transcription of the endoxylanse gene in its natural, non-transformed genome, heterologous promoters of the invention include, for example, non-endoxylanase associated promoters such as the alpha-amylase promoter and others.

A promoter is a DNA sequence that directs the transcription of a structural gene. Typically, a promoter is located in the 5' region of a gene, proximal to the transcriptional start site. A promoter may be inducible, increasing the rate of transcription in response to an agent, or constitutive, whereby the rate of transcription is not regulated by an inducing agent. A promoter may be regulated in a tissue-specific or tissue-preferred manner, such that it is only active in transcribing the operably linked coding region in a specific tissue type or types, for example, plant seeds, leaves, roots, or meristem. An heterologous promoter may initiate transcription of an operably linked gene coding sequence at an earlier time or developmental stage in a given tissue, than initiated by the native promoter of the same gene. Within a given host cell or tissue, certain promoters may drive transcription more strongly, resulting in a higher accumulation of transcript, thereby enhancing synthesis of the gene product.

A promoter useful in the invention is operably linked to a nucleotide sequence encoding endoxylanase such that transcription of the endoxylanase sequence is driven by the promoter. Optionally, the promoter is operably linked to a nucleotide sequence encoding a signal peptide, wherein the signal peptide is operably linked to the endoxylanase.

Many different promoters can be used to express the barley endoxylanase gene in a host cell. Of particular value in the present invention is a tissue-specific promoter which drives gene expression in aleurone tissue of cereal kernels at an early stage of germination and malting, such that endoxylanase activity accumulates in the kernel and enhances the degradation of cell wall polysaccharides. As used in the context of this invention, an "early promoter" includes promoters that are active from an early stage of germination and malting. Examples of suitable "early promoters" include, but are not limited to, the high pI α-amylase promoter (GenBank Acc. No.: J0420; Rogers, et al., 1985, *J. Biol. Chem.* 258:8169–8174), the Gbl2 gene promoter (GenBank Acc. No: M62740; Wolf, 1991, *Plant Physiol.* 96: 1382–1384) or the EPB1 or EPB2 gene promoters (GenBank Acc. No: U19359 and U19384. Mikkonen, et al., 1996, *Plant Mol. Biol.* 31: 239–254).

Temporal regulation of transcription can be achieved using an inducible promoter. In some situations, it may be desirable to induce expression of the endoxylanase gene by treating kernels with an inducing agent during steeping and malting. Known inducible promoters include the ACE1 system, which responds to copper (Mett, et al., 1993, *Proc. Natl. Acad. Sci.* 90:4567–4571). Preferred promoters, however, are barley promoters from the high pI α-amylase, Gbl2, EP-B 1 and EP-B2 genes, because these promoters are responsive to gibberellic acid, a natural plant phytohormone, in addition to being under endogenous control which determines both the temporal and tissue specificity of their activity.

In alternative applications, it may be desirable to accumulate endoxylanase activity in kernels during development, for example, in feed preparations or brewing adjuncts. In this instance, endosperm tissue-specific promoters would be preferable. Examples of suitable endosperm tissue-specific promoters include the hor3 promoter (Sørensen, et al., 1996 *Mol. Gen. Genet.* 250:750–760) and the hor3 promoter (Entwistle, 1988, *Carlsberg Res. Commun.* 53:247–258).

Early Promoters in Brewing

Commercial brewing processes utilize grains which are naturally low in fermentable sugars. During the malting and mashing process, cereal grain starch is degraded to sugars useful in the subsequent fermentation process. In the malting process, the grain is generally wetted and allowed to germinate, during which specific hydrolases are produced, including anylases, proteases, endoxylanases and β-glucanases. To minimize the duration of malting and improve the quality of the malt and thereby increase the efficiency of the brewing process and the quality of the final product, enhanced production of the degradative enzymes is beneficial.

As demonstrated in the Examples below, the timing of specific enzyme production by the germinating grain can be improved by operatively linking a nucleic acid sequence encoding a desired enzyme to an early promoter. An early promoter is active early in the germination process, such that the desired enzyme is expressed during the first days of malting.

Gene constructs including genes encoding hydrolytic enzymes such as endoxylanases, β-glucanases and amylases and operatively linked (driven by) an early promoter are used to transform cereal grain cells and plants such that during germination of the grain, production of the hydrolytic enzymes is enhanced. Preferably, production of the hydrolytic enzymes is at an earlier time in the process than production of the naturally produced enzyme. Most preferably, production of the enzymes is early and sustained such that enhanced amount of enzymes accumulate in the malt to enhance degradation of cell wall polysaccharides and starch during the brewing process.

Examples of useful early promoters include the high pI α-amylase promoter (amy-2)(Gen Bank Acc. No. J 0420), the Gbl2 gene promoter (Gen Bank Acc. No. M62740); and the EPB1 and EPB2 gene promoters (Gen Bank Acc. No. U 19359 and U 19384).

Additional Regulatory and Targeting Elements

Additional regulatory elements include terminators, polyadenylation sequences, and nucleic acid sequences encoding signal peptides that permit localization within a plant cell or secretion of the protein from the cell. Such regulatory elements include, but are not limited to, 3' termination/ polyadenylation regions such as those of the *Agrobacterium tumefaciens* nopaline synthase (nos) gene (Bevan, et al., 1983, *Nucl. Acids Res.* 12:369–385); the rubisco rbcs gene from *Pisum sativum* (Coruzzi et al., 1984, *EMBO, J.* 3:1671–1679); the potato proteinase inhibitor II (PINII) gene (Keil, et al., 1986, *Nucl. Acids. Res.* 14:5641–5650); and An et al., 1989, *Plant Cell* 1:1 15–122). Methods for adding or exchanging these elements with the regulatory elements of the endoxylanase gene are known.

Gene Transformation Methods

Numerous methods for introducing foreign genes into plants, such as biological and physical plant transformation protocols, can be used to insert the endoxylanase gene into a plant host. See, for example, Miki, et al., 1993, "Procedure for Introducing Foreign DNA into Plants", In: *Methods in Plant Molecular Biology and Biotechnology,* Glick and Thompson, eds., CRC Press, Inc., Boca Raton, pages 67–88. The particular method may vary depending on the host plant. Suitable methods include chemical transfection methods such as the use of calcium phosphate, microorganism-mediated gene transfer such as transfection using an Agrobacterium-mediated transfection system (Horsh, et al., 1985, *Science* 227:1229–31), electroporation, microinjection, and biolistic bombardment.

Expression vectors and in vitro culture methods for plant cell or tissue transformation and regeneration of plants are known and available. See, for example, Gruber, et al., 1993, "Vectors for Plant Transformation" In: *Methods in Plant Molecular Biology and Biotechnology,* Glick and Thompson, eds., CRC Press, Inc., Boca Raton, pages 89–119.

Agrobacterium-Mediated Transformation

The most widely used method for introducing an expression vector into plants is based on the natural transformation system of Agrobacterium. *A. tumefaciens* and *A. rhizogenes* are plant pathogenic soil bacteria which genetically transform plant cells. The Ti and Ri plasmids for *A. tumefaciens* and *A. rhizogenes,* respectively, include genes responsible for this genetic transformation. See, for example, Kado, 1991, *Crit. Rev. Plant Sci.* 10:1. Descriptions of the Agrobacterium vector system and methods for Agrobacterium-mediated gene transfer are provided in Gruber, et al., supra; Miki, et al., supra; and Moloney, et al., 1989, *Plant Cell Reports* 8:238. This transformation method has primarily been successful in transforming dicotyledonous plants. The development of new Agrobacterium binary vectors has recently extended the application of this transformation method to certain important cereal crops including rice (Hiei, et al., 1994, *The Plant Journal* 6:271–282) and maize (Yuji, et al., 1996, *Nature Biotechnology* 14:745–750).

Direct Gene Transfer

Since the major cereal crop species have, until recently, been found recalcitrant to Agrobacterium-mediated transformation, alternative methods of plant transformation, collectively referred to as direct gene transfer, have been developed.

A generally applicable method of plant transformation is microprojectile-mediated transformation, wherein DNA is carried on the surface of microprojectiles measuring about 1 to 4 μm in diameter. The expression vector is introduced into plant tissues with a biolistic device that accelerates the microprojectiles to speeds of 300 to 600 m/s, sufficient to penetrate the plant cell walls and membranes. (Sanford, et al., 1987, *Part. Sci. Technol.* 5:27; Sanford, 1988, *Trends Biotech* 6:299; Sanford, 1990, *Physiol. Plant* 79:206; and Klein, et al., 1992, *Biotechnology* 10:268). The application of this method for the transformation of barley has been reported (Wan and Lemaux, 1994, *Plant Physiol.* 104:37–48) and is currently one of the preferred methods for the transformation of cereals.

Another method for physical delivery of DNA to plants is by sonication (Zang, et al., 1991, *Bio/Technology* 9:996). Alternatively, liposome or spheroplast fusions have been used to introduce expression vectors into plants. See, for example, Deshayes, et al., 1985, *EMBO J* 4:2731; and Christou, et al., 1987, *Proc. Natl. Acad. Sci. USA* 84:3962. Direct uptake of DNA into protoplasts using $CaCl_2$ precipitation, polyvinyl alcohol or poly-L-ornithine have also been reported. See, for example, Hain, et al., 1985, *Mol. Gen. Genet.* 199:161; and Draper et al., 1982, *Plant Cell Physiol.* 23:451.

Electroporation of protoplasts and whole cells and tissues has also been described. See, for example, D'Halluin, et al., 1992, *Plant Cell* 4:1495–1505; and Spencer et al., 1994, *Plant Mol. Biol.* 24:51–61.

Endoxylanase Assay Methods

Transgenic plant cells, callus, tissues, kernels, and transgenic plants are tested for the presence of the endoxylanase gene by DNA analysis (Southern blot or PCR) and for expression of the gene by immunoassay or by an enzyme activity assay.

RNA and DNA Analysis of Endoxylanase Gene and mRNA

Using standard techniques, transgenic plant cells or tissue can be assayed for the presence of endoxylanase mRNA transcripts by hybridization to endoxylanase DNA probes. For example, the 867 bp EcoRI fragment of pS0083 [Sequence ID No. 6] is a useful hybridization probe for identifying the presence of endoxylanase mRNA in a test sample. Transcripts from plant tissue transformed with a construct comprising the endoxylanase gene fused to heterologous 5' or 3' UTR sequences can be selectively detected and quantitated by RNA-PCR using primers pairs located in the coding region and the 5' or 3' UTR.

An endoxylanase gene construct, fused to a heterologous promoter and/or terminator, can be detected in transformed tissue by PCR using primer pairs located in the endoxylanase coding region and the heterologous promoter or terminator sequences. The PCR product can be used as a hybridization probe for Southern blot analysis of genomic DNA from transformed plants. Transformed plants are compared with untransformed plants to distinguish the introduced constructs from the endogenous endoxylanase gene.

ELISA Assay for Endoxylanase

Transgenic cells, tissue or plants are screened for expression of the pro-endoxylanase and mature endoxylanase by immunological assays, including an Enzyme Linked Immunoassay (ELISA). Polyclonal antibodies used in an ELISA are, for example, generated against the purified barley endoxylanase (See Example 1).

Many variations of ELISA are known. In one representative type of ELISA, wells of a microtiter plate are coated with anti-endoxylanase antibodies. Fresh tissue (such as germinating kernels) is homogenized and centrifuged. An aliquot of the homogenized tissue (the antigen) is added in serial dilution to each anti-endoxylanase antibody coated well. Labeled anti-endoxylanase antibodies, such as biotinylated anti-endoxylanase antibodies, are then added to the microtiter plate. The concentration of bound labeled (biotinylated) antibody is determined by the interaction of the biotin with avidin coupled to peroxidase. The activity of the bound peroxidase is easily determined by known methods. The amount of endoxylanase in a tissue sample is quantitated with reference to the ELISA performed with pure antigen, where the detection range should lie in the range of 0.2–10 ng/ml. Any known method for producing antibodies and using such antibodies in an ELISA assay can be used to determine the amount of pro-endoxylanase expressed in transgenic plant cells and tissues of the invention.

Endoxylanase Activity Assay

Assay of endoxylanase activity is accomplished by reacting an enzyme sample with a suitable substrate, such as Birchwood AZCL-xylan or wheat AZCL-arabinoxylan (MegaZyme, Australia) and measuring the rate of degradation as described by the manufacturers.

Host Cells

Suitable host cells for transformation with the genomic endoxylanase gene of the invention or its coding sequence include cells that will benefit from the expression of enhanced amounts of endoxylanase. Host cells may be adapted for the production, isolation and purification of large amounts of endoxylanase. Preferred host cells include plant cells, such as barley or other cereal grains, that utilize endoxylanase for degrading xylan in a commercial process, such as beer production.

Host cells such as a bacterial, yeast or eukaryotic cell line are transformed with the genomic sequence encoding the endoxylanase of the invention such that the transformed cells produce enhanced levels of active endoxylanase. The active endoxylanase is then added to a brewing mixture, for example, during mashing to enhance degradation of arabinoxylans.

In a preferred embodiment of the invention, the genomic nucleic acid sequence encoding barley endoxylanase is used to transform plants whose grain are used in fermentation processes, including barley, wheat, sorghum and other cereals. Other host cells including bacteria, yeast, and eukaryotic cell lines are transformed with the genomic nucleic acid sequence encoding barley endoxylanase, and used to produce an active endoxylanase that can be added during beer production.

Method of Degrading Xylan

The invention is also directed to a method of degrading xylan using a recombinant endoxylanase. In a preferred embodiment, enhanced degradation of cell wall xylan is achieved by transforming plant cells with genomic barley endoxylanase DNA encoding a 62 kDa endoxylanase protein. Preferably, transcription of the endoxylanase gene is driven by a strong promoter which is specifically active in aleurone tissue during the first days of malting or germination. An example of such a promoter is the high pI α-amylase promoter. It is believed that plants transformed with the chimeric DNA genomic sequence (α-amylase promoter and barley endoxylanase coding sequence) will demonstrate enhanced production of endoxylanase in kernels in the first days of both malting and germination, in contrast to the kernels of non-transformed plants.

Cell wall or arabinoxylan degradation is also achieved by transforming alternate host cells, such as bacteria, yeast, or eukaryotic cells with the genomic endoxylanase such that the host cell produces an active endoxylanase that is added during brewing, for example, during mashing. Addition of supplementary endoxylanase during beer production can reduce wort viscosity and increase wort filtration rates, and thereby increase the production yield (see, for example, European Patent Application 0 227 159 A2).

Use of Barley Endoxylanase in the Production of Beer

The invention provides for improvements in the production of beer, particularly in the quality of the malt, the filterability and yield of the wort.

Beers are manufactured from grains, including barley grains, which are naturally low in fermentable sugars. Hydrolysis of starch to sugars is needed prior to fermentation with yeasts. To effect this hydrolysis, grains are wetted and allowed to germinate, during which time the germinating kernels produce hydrolytic enzymes. Among these hydrolases are cell wall polysaccharide hydrolytic enzymes, which bring about endosperm cell wall degradation, and, in turn, determine the degree of modification, an important malt quality parameter. The presence of undegraded arabinoxylan and β-glucan in the malt has a negative impact on the filtration and fermetable extract of the wort. At the end of malting, the malt is kilned and stored. The malt is then ground and suspended in water at the start of mashing, during which the major part of starch hydrolysis occurs.

Enhancing the availability of hydrolytic enzymes during malting and mashing enhances cell wall degradation and the yield of fermentable sugars and total extract derived from the degradation of starch. Enhanced availability includes providing enhanced amounts of specific enzymes, providing specific enzymes earlier in the malting process than naturally available, maintaining the active enzyme in the malt for a longer duration than naturally available, and a combination of these. Preferably, enzyme availability is enhanced by transforming cereal grain plants with a gene construct expressing a desired hydrolytic enzyme early in the malting process.

According to the invention, arabinoxylan degradation is enhanced during malting by the use of a cereal grain, such as barley, that has been transformed with the genomic nucleic acid sequence encoding barley preproendoxylanase. Preferably, the sequence encoding the genomic endoxylanase is operably linked to an early promoter, such as the α-amylase promoter which is active during the early stages of germination, to produce enhanced amounts of endoxylanase during malting.

During mashing, hydrolysis of starch occurs, including degradation of any residual arabinoxylans. Active endoxylanase is added to the mash to enhance further degradation of the endosperm cell wall. In an alternative embodiment of the invention, a host cell such as a bacterial, yeast or a eukaryotic cell line, is transformed with the nucleic acid sequence encoding the proendoxylanase of the invention such that large amounts of active endoxylanase are produced for combination with the malt during mashing. The added endoxylanase is produced in host cells transformed with the genomic sequence.

Most preferably, the cereal grain used in the brewing process is obtained from plants transformed with the genomic sequence and expressing enhanced amounts of endoxylanase in the grain.

EXAMPLES

The invention may be better understood by reference to the following examples, which serve to exemplify the invention and are not intended to limit the scope of the invention in any way Example 1

Time Course of Endoxylanase Expression in Germinating Barley

Late and poor induction of endoxylanases in germinating and malting barley was demonstrated by Western and Northern blot analyses of the naturally expressed enzyme in germinating barley cells. Triumph barley was sterilized with silver nitrate as described by Slade, et al., 1989, supra, and soaked for 12 hours in a water solution containing nystatin (20 μg/ml), chloramphenicol (10 μg/ml) and ampicillin (50 μg/ml). The kernels were germinated on filter paper, in the same water solution, at 15° C. in the dark. Samples were collected every 24–48 hours over a period of 14–16 days, and the shoots and roots discarded prior to further analysis.

In a 3.5 kg micromalting process, after a first wet steep of 8 hours, followed by a dry period of 16 hours, a second steep was performed up to 45% moisture. Subsequently, the barley was germinated at 16–17° C. Samples were taken every 24 hours after steep-in.

Sample Preparation

Cellular proteins were extracted from samples of barley taken during a time course of germination and micromalting. The samples were prepared by homogenizing 5 kernels in a Ultra Turrax T25 in 2 ml of 50 mM sodium malate pH 5.2, 50 mM NaCl, 2 mM $CaCl_2$, 3 mM $NaN_3$. The samples were then centrifuged. After the addition of BSA to 0.1%, the supernatant was assayed for enzyme activity.

The following protocol is used to purify processed mature endoxylanase to later raise antibodies against the mature endoxylanase, to provide a standard for determining enzyme activity and for SDS-PAGE and Western blotting. 150 g of kernels, germinated for 14 days (see above) were homogenized in a Waring blender for 3 minutes in two volumes of 50 mM sodium acetate, pH 5.0, 5mM sodium azide, 10 mM EDTA, 3 mM 2-mercaptoethanol, and 3 mM phenylmethylsulphonyl fluoride (PMSF) at 0° C. After a 20 minute incubation on ice, insoluble material was removed by centrifugation. The extract was then subjected to fractional precipitation with 20–40% ammonium sulfate. The precipitated material was resuspended in extraction buffer, desalted on a Sephadex G-25 coarse column (Pharmacia), and equilibrated in 50 mM sodium acetate, pH 5.0, 5 mM sodium azide and 3 mM PMSF. The de-salted extract was concentrated to a volume of 4.8 ml, with a protein concentration of 2–4 mg/ml, by ultrafiltration with a YM-10 membrane (Amicon). The preparation was then diluted with 15 ml of 20 mM Bis-Tris/HCl pH 6.2 and applied to a 1 ml MONO Q HR5/5 FPLC column (Pharmacia), at a flow rate of 1 ml/minute in the same buffer. After washing with 5 ml of buffer, the protein was eluted with a 25 ml linear (0–0.35 M) NaCl gradient at a flow rate of 0.5 ml/min. Endoxylanase activity, measured by the above described methods, peaked in protein fractions eluting at 0.9–1.2 M NaCl. These fractions were pooled (2 ml) and subjected to gel filtration on a 24 ml Fractogel HW 50-superfine (Merck) HR 10/30 column (Pharmacia), equilibrated in 20 mM Bis-Tris/HCl pH 6.2, 0.1 M NaCl, with a flow rate of 0.2 ml/minute. Endoxylanase activity eluted with a single protein peak in the 8–10 ml elution fractions. The peak fractions were diluted with 10 ml 20 mM Bis-Tris/HCl pH 6.2 and applied to the MONO Q column to concentrate the sample to 30 μg protein in 0.5 ml.

Figure 2:
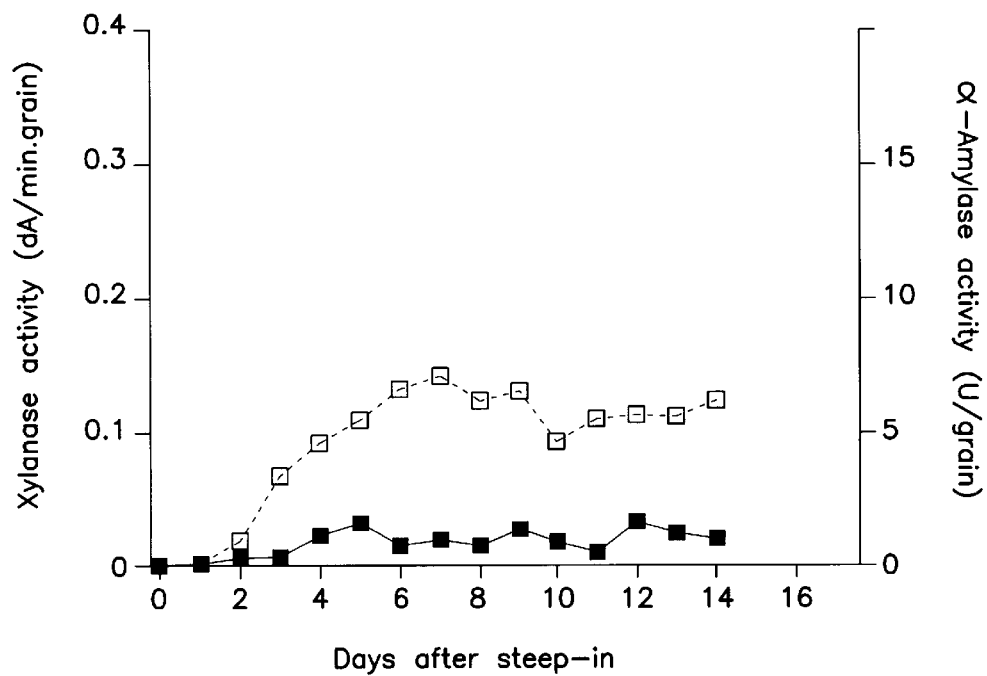
FIG. 2 is a graph showing the time course of α-amylase and endoxylanase enzyme activities during the process of micromalting.

The final preparation of the 34 kDa barley endoxylanase was 90% pure, as judged by SDS-PAGE and silver staining. The N-terminal amino acid sequence of the purified 34 kDa endoxylanase (~150 pmol protein) was determined by Edman degradation (Eurosequence B. V., Groningen, The Netherlands). The determined sequence is indicated in FIGS. 9 and 12 in an alignment with the deduced sequences of the endoxylanase cDNA and genomic open reading frames (ORFs). Although computer analysis for putative glycosylation sites predicted 4 glycosylation events in the 34 kDa endoxylanase, the preparation, after separation on Servalyt PreNets gel (Serva), was found not to be glycosylated according to the PAS negative reaction using the method of Zacharius and Zell, 1969, Anal. Biochem., 30:148–152.

α-Amylase Activity

α-Amylase activity was measured in germinated and malted barley kernel extracts. The extracts were prepared in the same manner as the extracts for the measurement of endoxylanase activity, described above, but with the addition of BSA to 0.02%. α-Amylase activity during germination and micromalting was determined using a commercially available assay (MegaZyme kit; MegaZyme, Australia), according to the method described in McCleary and Sheehan, 1987, "Measurement of Cereal α-amylase: A New Assay Procedure", *J. Cereal Sciences* 6:237–251, and adapted for use in microtiter plates as described in Soor and Hinke, 1990, *Anal. Biochem.* 188:187–191. As shown in FIGS. 1 and 2, during both germination at 15° C. and micromalting, α-amylase activity was detected as early as day two, reaching a plateau in activity at approximately day eight, and continuing through the tested germination period (16 days) and micromalting period (14 days). Maximal α-amylase activity was lower during micromalting than germination, but exhibited a similar temporal pattern in activity.

Endoxylanase Activity

To determine endoxylanase activity during germination and micromalting, samples were assayed for their ability to degrade xylan. Samples were equilibrated in a solution containing 50 mM sodium malate pH 5.2, 50 mM NaCl, 2 mM $CaCl_2$, 3 mM $NaN_3$, 0.1% BSA. 6 mg Birchwood AZCL-xylan (MegaZyme, Australia) was added, as a substrate, to 0.2 ml sample and incubated at 45° C. for 60 minutes. Under these conditions green malt produced a linear rate of xylan degradation over a period of 2 hours. The reaction was stopped by the addition of 1.8 ml 1% w/v Tris. After filtration of the assay mixture, absorbance was read at 595 nm. The amount of endoxylanase activity was calculated as the change in absorbance with time (minutes) per grain and is shown in the figures as dA/min. grain.

In contrast to α-amylase activity, endoxylanase activity developed much later during germination, reaching a maximum by day 15 (FIG. 1). During prolonged micromalting endoxylanase activity was barely detectable (FIG. 2).

Northern Blotting

Northern blots were made to determine if late accumulation of endoxylanase activity was due to late induction of gene transcription. RNA was isolated from barley according to the method described in Hensgens, et al., 1989, *Rice Genetics Newsletter*, 6:163–168. For each sample, 15 μg of total RNA was denatured using glyoxal/DMSO and separated on a 1.2% agarose-gel, as described in Sambrook, et al., 1989, *Molecular Cloning: A Laboratory Manual*, section 7.40. Northern blotting was performed using GeneScreen Plus membranes according to the manufacturers instructions (DuPont).

Radioactive-labeled cDNA probes were prepared using the Oligolabelling kit from Pharmacia. An α-amylase cDNA probe [Sequence ID No. 7] was prepared by isolating a 788 bp SacI fragment from plasmid pM/C (Rogers, et al., 1985, *J. Biol. Chem.*, 258:8169–8174). An endoxylanase probe [Sequence ID No. 6] was prepared by isolating a 867 bp EcoRI of the pS0083 cDNA clone. As a control, for equal loading of the lanes, the blots were rehybridized with a wheat ribosomal DNA probe pTA 17 (Gerlach and Bedbrook, 1979, *Nucleic Acids Res.*, 7:1869:1885).

Figure 3:
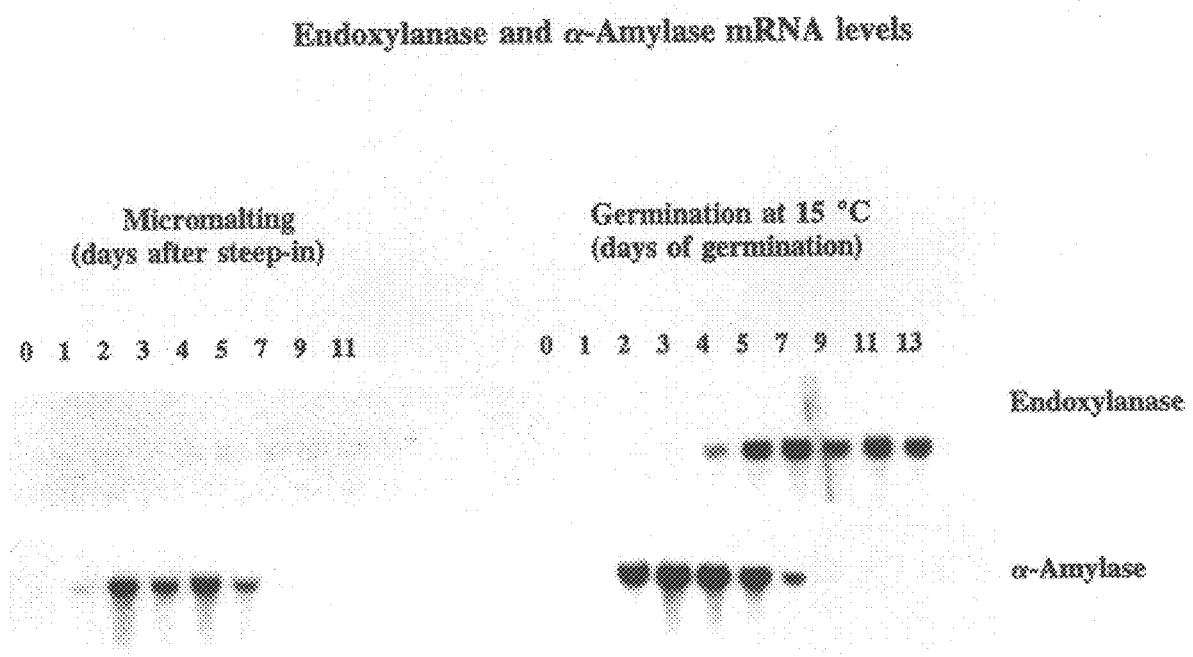
FIG. 3 is a Northern blot used to detect endoxylanase and α-amylase mRNA present in RNA extracted from Triumph barley kernels sampled during micromalting or germination. An 867 bp EcoRI fragment from cDNA clone pS0083 was used as an endoxylanase probe and a 788 bp SacI fragment from plasmid pM/C (Rogers, 1985, *J. Biol. Chem.*, 260:3731–3738) was used to detect the α-amylase messenger.

In Northern blots of Triumph barley samples taken during germination, α-amylase mRNA was already clearly detectable at day two. In contrast, endoxylanase transcripts could not be detected until day four (FIG. 3). In the samples taken during micromalting, α-amylase mRNA was readily detectable from day 3 onwards while no endoxylanase mRNA could be detected. (FIG. 3).

The data indicates that endoxylanase is induced at a significantly later stage of germination than α-amylase, and that the retarded induction can be ascribed to a delay in transcription. Furthermore, during malting, the extremely low induction of the endoxylanase activity can be ascribed to limited transcription of the endoxylanase gene. In these experiments, no induction of the endoxylanase was observed during malting.

Western Blotting

To study the induction of endoxylanase at the protein level, Western blots were probed with a polyclonal antiserum raised against 34 kDa endoxylanase (Xyl-Bar-PC) and with a polyclonal antiserum against a synthetic peptide [Sequence ID No. 5] comprising the N-terminal 30 amino acids of the 41 kD endoxylanase (Xyl"N"-Bar-PC).

To produce the polyclonal antiserum, Xyl-Bar-PC, a New Zealand white rabbit was immunized subcutaneously with 100 μg of purified endoxylanase dissolved in 2 ml of an emulsion consisting of equal volumes of PBS and complete Freund's adjuvant. The endoxylanase was chromatographically purified from germinated barley and had a calculated protein content 0.1–0.5 mg/ml. Subsequently, three boosters were administered (100 μg of the purified endoxylanase preparation dissolved in 2 ml of equal volumes of PBS and incomplete Freund's adjuvant). The titer of the preimmune serum was <1:250. Following the second booster a 50% titer was 1:16,000. Following the third booster, the titer was 1:40,000.

Barley kernels were collected during germination and micromalting and frozen and stored at −80° C. The kernels were ground in 5× concentrated sample buffer (Laemmli, 1970, *Nature*, 227:680–695), incubated for 5 min. at 100° C. and centrifuged for 15 min. at 12000×g. Aliquots of the supernatant were analyzed by polyacrylamide gel electrophoresis (SDS-PAGE), using 12.0% gels, according to Laemmli (1970). Gels were silver stained according to Blum, et al., 1987, *Electrophoresis*, 8:93–99.

For Western blotting, the separated proteins were transferred from the gels onto nitrocellulose membranes (Schleicher and Scheull) by semi-dry electroblotting essentially as described by Towbin, et al., 1979, *Proc. Natl. Acad. Sci. USA* 76:4350–4354. After blotting, the nitrocellulose membranes were soaked for 0.5 hours in phosphate buffered saline containing 0.05% (v/v) Tween 20 (PBST) plus 1% (w/v) BSA and incubated overnight at 25° C. with the polyclonal antiserum (Xyl-Bar-PC) diluted (1:2000) in the same buffer.

After incubating overnight with the polyclonal antiserum, the membranes were washed with PBST and incubated for at least 1 hour at 25° C. with goat anti-rabbit IgG conjugated to alkaline phosphatase. The bound alkaline phosphatase activity was visualized by adding 5-bromo-4-chloro-3-indolyl-phosphate/nitro blue tetrazolium in 100 mM Tris/HCl pH 9.5, 100 mM NaCl and 5 mM $MgCl_2$. Color development was stopped by washing the nitrocellulose membranes with distilled water.

Figure 4:
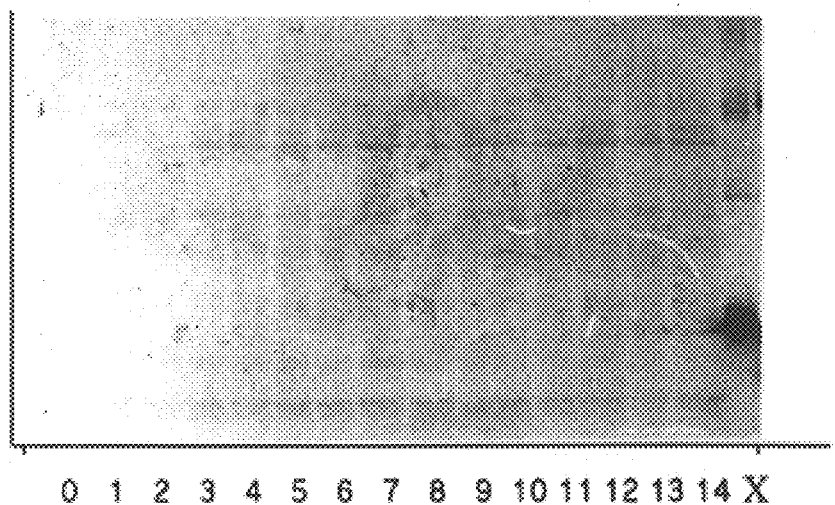
FIG. 4 is a Western blot used to detect endoxylanase in extracts of Triumph barley kernels sampled during micromalting. The gel-separated protein extract was probed with anti-xylanase antibody (Xyl-Bar-PC) raised against the 34 kDa barley endoxylanase. The lane marked with an "X" contained purified 34 kDa endoxylanase as a control.
Figure 5:
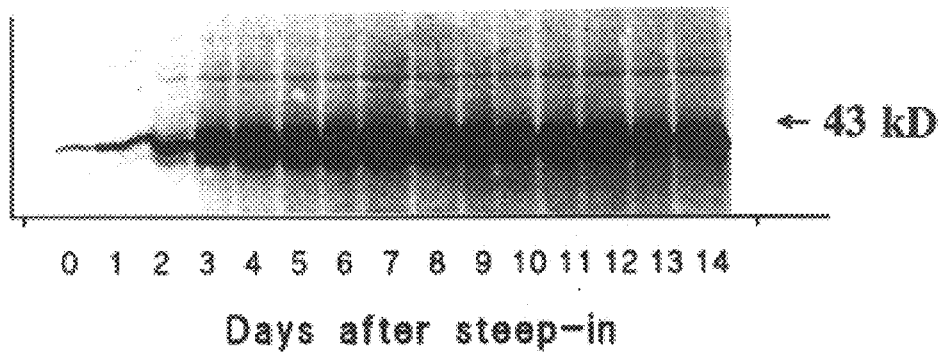
FIG. 5 is a Western blot used to detect the presence of α-amylase in extracts of Triumph barley kernels sampled during micromalting. The gel-separated protein extract was probed with anti-α-amylase antibody.

FIGS. 4 and 5 show a Western blot of samples taken during micromalting. The blot in FIG. 4 was probed with Xyl-Bar-PC polyclonal antiserum. A duplicate blot (FIG. 5) was probed with a polyclonal antiserum against α-amylase isoenzyme 2 (Juge, et al., 1993, *Gene*, 130:159–166). Whereas the blot produced with the polyclonal antiserum against α-amylase shows a clear induction of α-amylase from day two of malting onwards, no significant endoxylanase levels were detected throughout malting (FIG. 4).

Figure 6:
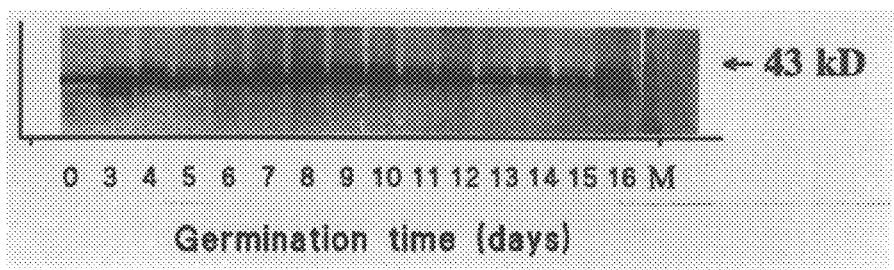
FIG. 6 is a Western blot used to detect α-amylase in extracts of Triumph barley kernels sampled during germination and probed with anti-α-amylase antibody.

A Western blot was also prepared from samples taken during germination at 15° C. (FIGS. 6–8). Using the Xyl-Bar-PC antiserum, the 34 kDa endoxylanase was first detected in samples taken after 10 days of germination (FIG. 7). Bands of higher molecular mass proteins (approximately 62, 54 and 41 kDa) reacted with the anti-endoxylanase antiserum in samples taken earlier during germination, starting at about day 3 (FIG. 7).

Endoxylanase activity was determined as described above, and is shown in FIG. 8 for easy comparison to the appearance of the different molecular mass forms of the endoxylanase in FIG. 7. The disappearance of the larger molecular mass forms of endoxylanase and the accumulation of the 34 kDa form during germination correlates with an increase in endoxylanase activity.

The 41 kDa band may correspond to the endoxylanase purified by Slade, et al., 1989, *Eur. J. Biochem.*, 185:533–539. However, higher molecular mass antiserum-reactive proteins indicate the existence of a larger precursor endoxylanase that is processed to form the mature 34 kDa endoxylanase.

The synthesis of barley endoxylanase in a precursor form is confirmed by the characterization of a cDNA clone pS400 [Sequence ID No. 8], which was identified among expressed sequence tags (ESTs) from a cDNA library made from 12 hour gibberellic acid-treated barley aleurone layers of cv. Himalaya kernels (Leah, et al., 1991, *Journal Biological Chemistry* 266:1564–1573). FIG. 9 shows the nucleotide sequence of pS400 and one open reading frame extending from the 5' end. The deduced amino acid sequence [Sequence ID No. 9] is also shown.

The determined N-terminal amino acid sequence of the 41 kDa endoxylanase, isolated by Slade, et al., 1989, *Eur. J Biochem.*, 185:533–539, and the N-terminal amino sequence of the purified 34 kDa endoxylanase can both be aligned with the deduced sequence of the pS400 cDNA clone. The N-terminal sequence of the 34 kDa endoxylanase lies down stream of the N-terminus of the 41 kDa endoxylanase in the deduced sequence. The ORF predicted for the 34 kDa mature endoxylanase encodes a protein of 348 amino acids with a molecular mass of 39 kDa. Since the ORF extends to the 5' end of the cDNA, it is very unlikely that the methionine residue located 32 amino acids upstream of the N-terminus of the 41 kDa endoxylanase, could function as the start methionine followed by a cleavable signal peptide. Furthermore, as shown above, the 34 kDa endoxylanase antibody (Xyl-Bar-PC) recognized additional larger precursor forms.

To confirm that the larger molecular mass forms (approximately 54, and 62 kDa) are indeed precursors of the 41 and 34 kDa forms of the endoxylanase, a Western blot of proteins extracted from 6 and 12 day germinated kernels (FIG. 10) was probed with the anti-xylanase antibody, Xyl-Bar-PC (described above) and a second polyclonal antiserum, Xyl"N"-Bar-PC. Xyl"N"-Bar-PC recognizes a synthetic peptide formed of the 30 amino acids of the N-terminal sequence published by Slade, et al., 1989, *Eur. J. Biochem.*, 185:533–539 and does not overlap with the 34 kDa region of the protein. Therefore, the two polyclonals are independent.

The antiserum Xyl"N"-Bar-PC, was produced against a synthetic peptide (VYPVDHKARF KQLKDKTDKA RKRDVILKLG-C) [Sequence ID No. 5]. The peptide was prepared by solid phase synthesis at TNO-PG (Leiden) using F-moc protected amino acids in an automated Milligen 9050 Continuous Flow Synthesizer (Millipore Co, Milford, Mass.). The peptide was purified, essentially as described by Zegers, et al., 1991, *Biochem. Biophys. Acta.* 1073:23–32, and the amino acid composition was confirmed as described by Janssen, et al., 1986, *Chromatographia*, 22:345–350. The peptide was then conjugated to keyhole limpet hemocyanin (KLH) using m-maleimidobenzoyl-N-hydroxysuccinimide (MBS) as a coupling agent reactive for the terminal cysteine residue added to the peptide (Boersma, et al., 1993, *Use of Synthetic Peptide Determinants for the Production of Antibodies* In: Immunohistochemistry II (A.C. Cuello, ed.) Wiley and Sons, Toronto, pp. 1–78).

Young adult New Zealand white SPF rabbits were immunized with 250 μg of the conjugate dissolved in 2 ml of an emulsion consisting of equal volumes of PBS and complete Freund's adjuvant. The rabbits were immunized three times at four week intervals. (Boersma, et al., 1992, *Res. Immunol.*, 143:503–512). The antisera reacted in ELISA with directly coated free peptide showing a final 50% titer of 1:1,600 and 1:3,200 for the two individual rabbits. In Western blotting a dilution of 1:500 was used.

Figure 10:
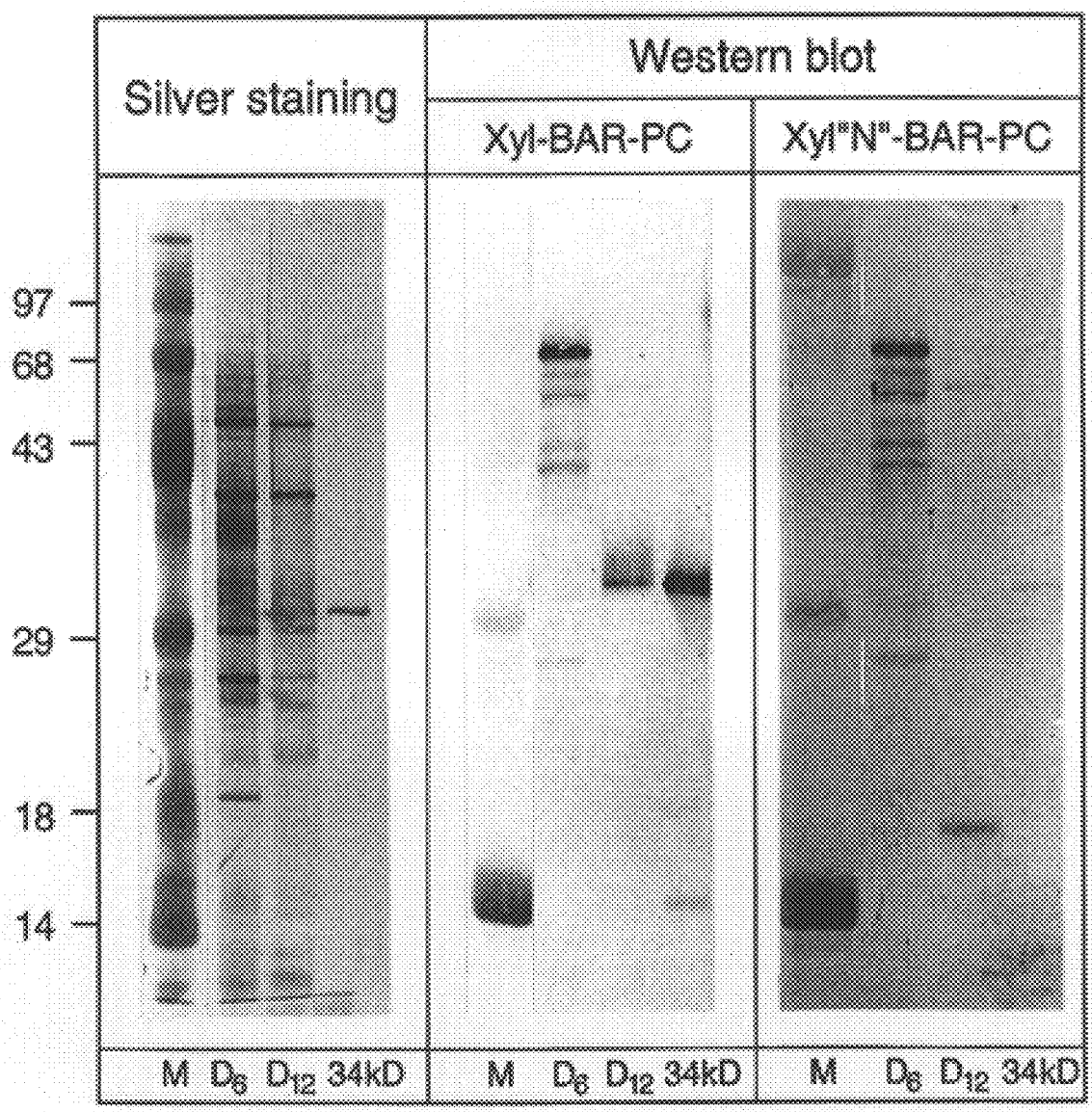
FIG. 10 is a silver-stained SDS-polyacrylamide gel and derived Western blot of endoxylanase from Triumph barley kernel extracts sampled during germination at day 6 ($D_6$) and day 12 ($D_{12}$). The Western blot was probed with two different anti-xylanase polyclonal antibodies: Xyl-Bar-PC, recognizing the 34 kDa endoxylanase; and Xyl"N"-Bar-PC, recognizing higher molecular mass forms of endoxylanase, including the 41 and 62 kDa forms. Xyl"N"-Bar-PC was raised against a synthetic peptide comprising the N-terminal 30 amino acids of the 41 kDa endoxylanase. M indicates molecular mass markers. "34 kDa" indicates purified 34 kDa barley endoxylanase control.

As shown in FIG. 10, the 62 kDa protein, present in a sample taken at day 6 of germination, clearly reacts with both antibodies, while the 34 kDa form, present at day 12, does not. This confirms that the 34 kDa endoxylanase is formed by the proteolytic removal of the N-terminal amino acids from the precursor proteins. The 54 and 41 kDa bands could be detected with both Xyl-Bar-PC and Xyl"N"-Bar-PC.

Additional experimentation was carried out to determine whether the early high MW forms of the endoxylanase were due to glycosylation. Computer analysis of the deduced amino acid sequence shows that the 34 kDa part of the endoxylanase contains four potential N-glycosylation sites. The purified 34 kDa enzyme, however, gave a negative reaction with the PAS stain in contrast to a positive reaction for the ovalbumin control (data not shown). This data indicates that the 34 kDa enzyme is not glycosylated.

In summary, protein analysis by Western blotting with anti-xylanase antibodies indicates that an endoxylanase of approximately 62 kDa is initially produced during germination and is processed during germination into smaller molecular mass forms.

Example 2

Size of the Endoxylanase and its Messenger RNA

To establish the size of the endoxylanase messenger RNA, barley was germinated for 6 days and the RNA was extracted and separated on agarose gels and hybridized with endoxylanase or α-amylase cDNA probes as described above.

The position of the endoxylanase band on the Northern blot was compared to the position of α-amylase as well as to RNA molecular mass markers (0.3–7.4 kb, Boehringer, Mannheim). The endoxylanase transcript was found to have a size of about 1.9 kb (FIG. 11). The α-amylase transcript showed the expected size of 1.5 kb (Rogers et al., 1983, *J. Biol. Chem.*, 258:8169–8174) (See FIG. 11). This data indicates that the endoxylanase mRNA is significantly larger than the mRNA for the 45 kDa α-amylase. The 0.4 kb extra length of the messenger indicates that the precursor endoxylanase protein would be about 60 kDa, confirming that the 34 kDa endoxylanase is formed from the 62 kDa precursor.

Example 3

Endoxylanase Genomic Sequence

Using a radiolabelled insert of pS400 cDNA as a probe, a genomic endoxylanase clone (xyl26) was isolated and screened from a barley genomic library of the cv. Igri cloned in the lambda Fix II Vector (Stratagene; LaJolla, Calif., U.S.A.). The coding region of the endoxylanase xyl26 gene lies within a 5529 bp Xba1 fragment shown in FIG. 13, subcloned from the isolated barley genomic clone. As shown in FIG. 13, the putative TATA box is positioned at nucleotide 1746. The first ATG, which lies 132 bp downstream of the TATA box (position 1877), as well as the stop codon (position 3719), are underlined. This ATG is in frame with the coding region for the 41 kDa and 34 kDa products and encodes a 62 kDa protein with an IEP of 5.6. The polyadenylation site is at position 3914. The nucleotide sequence from the TATA box and 3' downstream region is shown in FIGS 12A–D, where the coding sequence is shown in upper case.

Using this genomic sequence information, primers were made to identify the 5' end of the endoxylanase mRNA and to construct a full-length cDNA clone. FIG. 12 shows the relative positions of the sense (5' ACACAGCAGAGAT-CATCA 3') [Sequence ID No. 10] and antisense (5' ACGCG-GTAAGTGAGAC 3') [Sequence ID No. 11] primers which were used to amplify the 5' end of the-endoxylanase mRNA from an RNA extract of 6 day germinated kernels (Gene Amp RNA PCR kit; Perkin Elmer Cetus Norwalk, U.S.A.). Alignment and fusion of the overlapping RNA-PCR and pS400 cDNA sequences predicted an mRNA length of 1950 nucleotides without a poly A tail. By comparing the sequence of the PCR fragment to that of xyl26, a 83 bp intron (intron 1) was identified (see FIGS. 12A–D and 13). Moreover, comparison of the xyl26 genomic sequence and the pS400 cDNA sequence showed the presence of a 91 bp intron (intron 2) located between the regions encoding the N-termini for the 41 kDa endoxylanase (Slade, supra) and the 34 kDa xylanase (see FIGS. 12A–D and 13).

The 5' end of the endoxylanase mRNA was further examined by hybridizing endoxylanase mRNA with labeled PCR probes generated from defined sequences positioned at the 5' end of the endoxylanase gene, xyl26. The 5' end of the PCR probes were located in the promoter and extended to positions upstream of the TATA box (PCR.1 [Sequence ID No. 12] and PCR. 2 [Sequence ID No. 13]) or downstream of the deduced translation start site (PCR.3 [Sequence ID No. 14] and PCR. 4 [Sequence ID No. 15]), (see FIG. 13). As a control, the xylanase cDNA insert of pS0083 (FIG. 13) was used as a probe which would hybridize with the mRNA 3' end. All probes were shown to be equally labeled from their hybridization signal after hybridization with a Southern dot blot on which xyl26 DNA had been applied in a dilution series (FIG. 14).

A Northern blot of RNA from 5–7 day germinated kernels was then hybridized with the same PCR probes. As shown in FIG. 15, probes PCR.3 and PCR.4, as well as the pS0083 probe hybridized to the ~1900 nucleotides endoxylanase mRNA. Since neither PCR.1 or PCR.2 probes gave a hybridization signal, this confirms that the endoxylanase mRNA does not extend upstream of the predicted TATA box (position 1746). The calculated length of the endoxylanase mRNA (see above) is in agreement the Northern blot size determination of 1900 nucleotides from Example 2, (see FIG. 11). As discussed in Example 2, an mRNA of this length encodes a protein of about 62 kDa, confirming that barley endoxylanase is synthesized as a 62 kDa precursor protein.

Example 4

Analysis of Genomic Endoxylanase Copy Number
Southern Blotting Southern blot analysis was used to determine the number of endoxylanase genes in barley cv. Himalaya and Triumph related to the genomic and cDNA endoxylanase clones. The EcoRI insert of clone pS0083, which covers the 3' coding region of the gene, was used as a probe (See FIG. 13). A PCR-produced probe, [Sequence ID No. 16] which covers the 3' untranslated region of the endoxylanase transcript (3' UTR) was amplified from the pS400 cDNA clone, from position 1493 (at the stop codon) to position 1679 (5' of the poly A tail). The 3' UTR probes are generally found to give gene specific hybridization signals.

Figure 16:
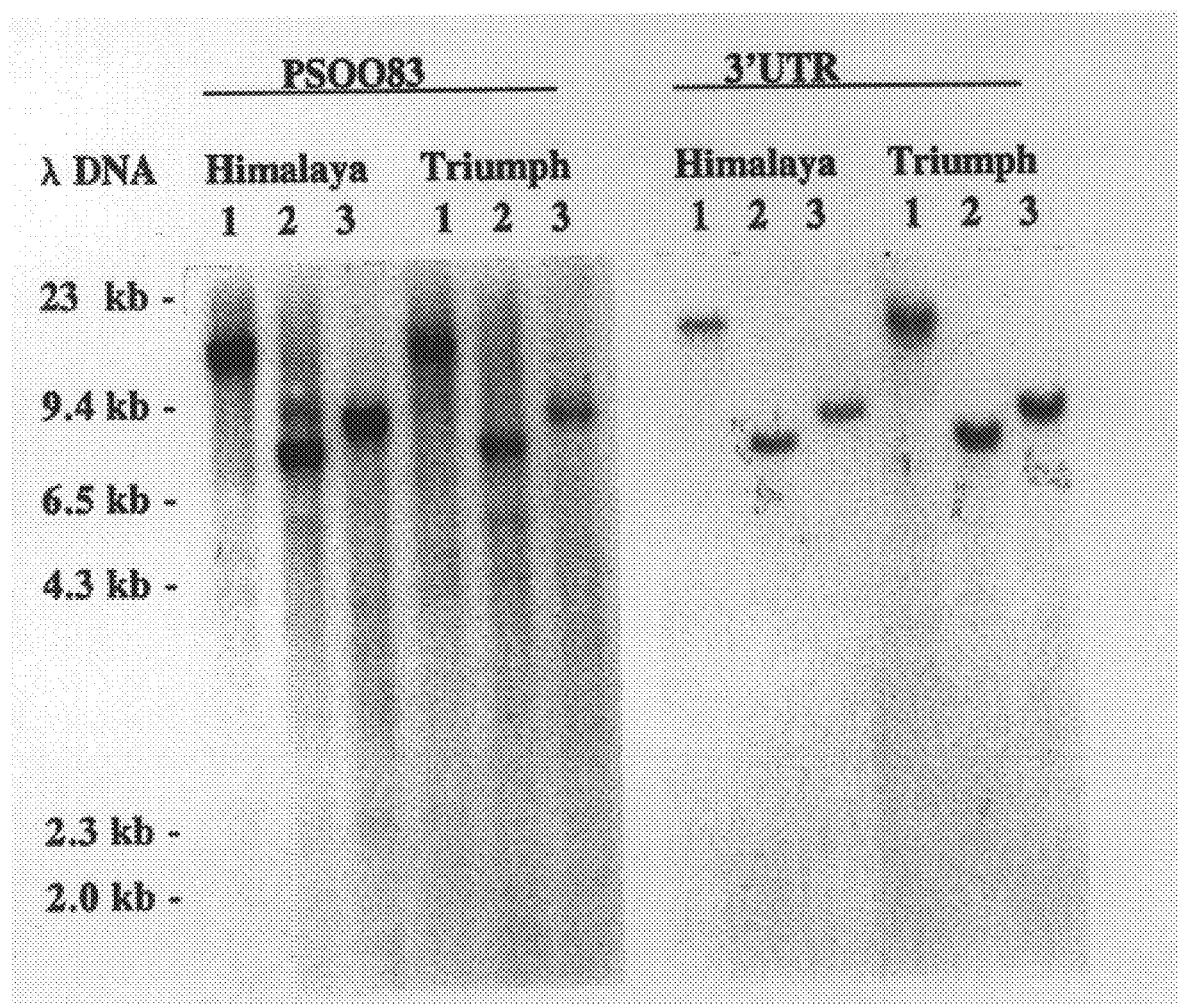
FIG. 16 is a Southern blot showing digested DNA from two barley varieties, Himalaya and Triumph. Lane 1—BamHI digest; Lane 2—BglII; lane 3—HindIII digest. The blots were probed with a labeled EcoRI insert of clone pS0083 or with a PCR-produced probe covering the 3' untranslated region of the messenger (3'UTR). (See FIG. 14 for probe position)

As shown in FIG. 16, a single clear band was obtained from the DNA samples of both barley varieties using each probe. Some weak bands were visible in all digests where pS0083 was used as a probe. In contrast, only a single hybridizing band was seen in each digest with the gene specific probe (3' UTR). This data indicates that the endoxylanase is a single copy gene in the barley genome and that there are no additional genes in the genome with high homology to the endoxylanase gene (xyl26).

Example 5

Transient Expression of Endoxylanase in Barley Aleurone Protoplasts

Secreted enzymes are commonly synthesized in precursor form, involving a signal peptide and propeptide which are required for transit through the endoplasmic reticulum, intracellular targeting, folding or activation of the polypeptide. To establish the importance of the full-length precursor form (61.4 kDa) for synthesis of an active barley endoxylanase, constructs encoding the full-length (61.4 kDa) and processed (41 and 34 kDa) forms were expressed in barley aleurone protoplasts and the level of endoxylanase activity was determined.

Transient Expression System

Protoplasts were isolated from aleurone layers of Hordeum vulgare L. cv. Himalaya (Dept. Agronomy, Washington State Univ.; Pullman, U.S.A.) by a method adapted from Jacobsen, et al., 1985, *Planta*, 163:430–438. Seeds (200) were de-embryonated, sterilized and quartered. The quartered seeds were then left in the dark to imbibe for 60 hours at 25° C. in 30 ml succinate buffer (20 mM $Na_2C_4H_4O_4$, pH 5.3, 20 mM $CaCl_2$, 5 µg/ml nystatin, 50 µg/ml ampicillin). After incubation, the endosperm was scraped off the aleurone layers and the aleurone layers were repeatedly washed with succinate buffer.

The aleurone layers were preincubated in the dark at 25° C. in 15 ml isolation medium (10 mM MES, 20 mM $CaCl_2$, 0.1M D-glucose, 0.35M mannitol, 0.385% (w/v) Gamborg B5 (Flow), 10 mM arginine, 1% (w/v) PVP K25, 4.5% (w/v) cellulase 'Onozuka'R10 (Yakult-Honsha Co., Japan), 5 µg/ml nystatin and 50 µg/ml ampicillin adjusted to pH 5.4 and 800 mOsm). As the first protoplasts were released, the aleurone layers were transferred to fresh medium and incubated for an additional 16 hours. The protoplasts were then released by washing the layers with 25 ml transfection medium (5 mM MES, 15 mM $MgCl_2$, 0.1M D-glucose, 0.556M mannitol adjusted to pH 5.6 and 800 mOsm). The protoplasts were then passed through a 100 µm sieve, washed 2 times with transfection medium and then suspended in transfection medium at a concentration of $5 \times 10^5$ protoplasts per ml.

Figure 17:
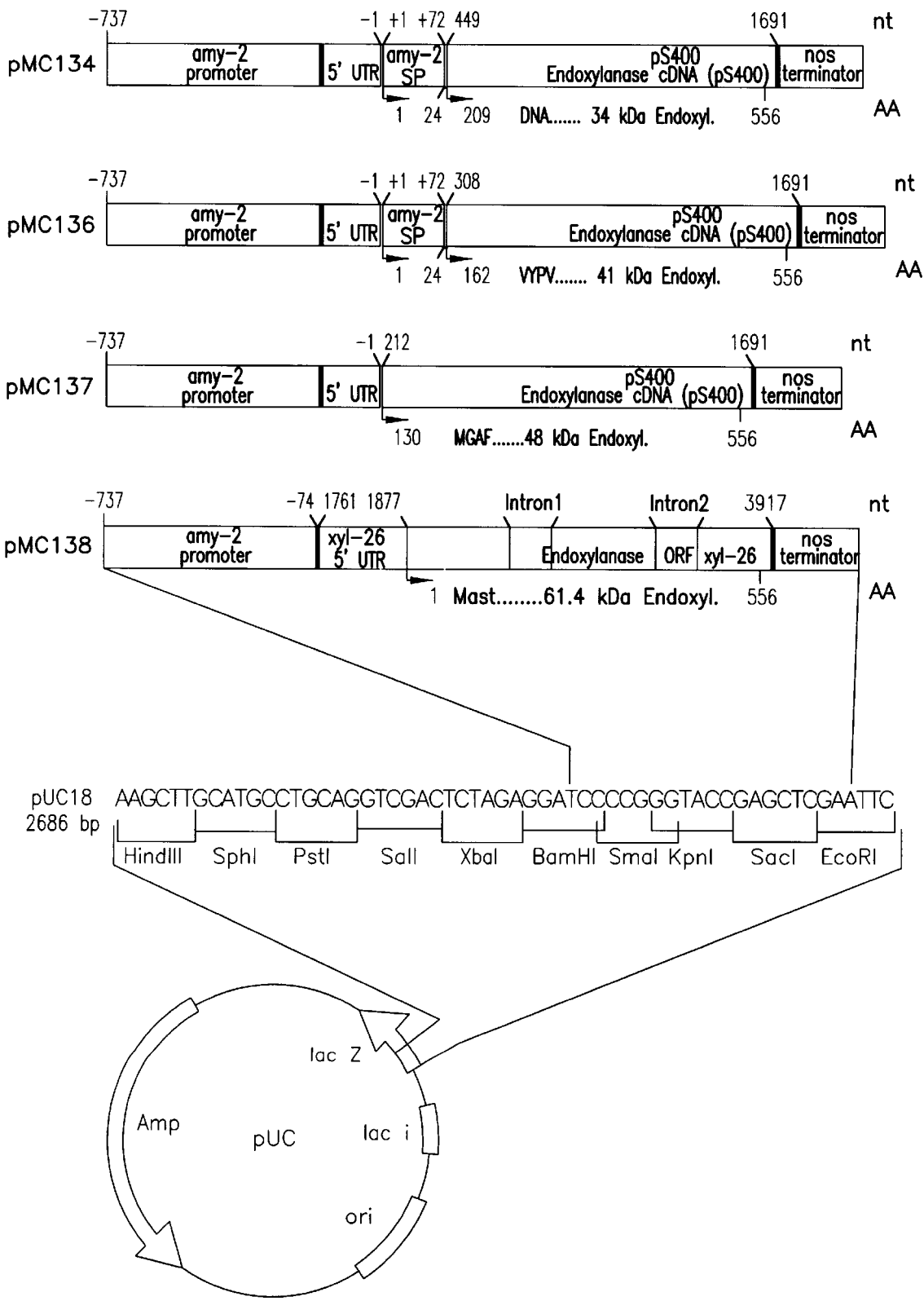
FIG. 17 is a diagram showing the construction of barley endoxylanase expression plasmids.

The transfection procedure was adapted from Lee, et al., 1989, *Plant Molecular Biology*, 13:21–29. Four barley endoxylanase plasmids were used in the transformation, the construction of which is shown in FIG. 17. The high pI barley α-amylase promoter [Sequence ID No. 17], amy-2 (−1/−737 upstream of the ATG, GenBank: J04203)(Rogers, 1985, *J. Biol. Chem.*, 260:3731–3738) was fused translationally to an open reading frame comprising a signal peptide and truncated portions of the nucleic acid sequence encoding barley endoxylanase, as shown in FIG. 17 (plasmids pMC134/136/137). The polyadenylation site of pS400 in the 3 constructs was fused by overlap extension PCR (Horton, et al., 1989, Gene 77:61–68) to the 3' UTR of the Nos terminator (nucleotides 1847–2101) [Sequence ID No. 18] (nos; GenBank: J01541) (Bevan, et al., 1983, Nuc. Acids. Res. 12:369–385).

Plasmid pMC134 includes both the amy-2 promoter and amy-2 signal peptide encoding sequence [Sequence ID No. 19] (amy-2 SP; +1/+172 GenBank: J04203) of the amy-2 gene, fused by overlap extension PCR to the truncated endoxylanase ORF [Sequence ID No. 20] encoding the 34 kDa endoxylanase product.

Plasmid pMC136 includes the amy-2 promoter and amy-2 signal peptide encoding sequences (described above) fused by overlap extension PCR to the truncated endoxylanase encoding the 41 kDa endoxylanase product [Sequence ID No. 21].

Plasmid pMC137 includes the amy-2 promoter sequence translationally fused, by overlap extension PCR, to the truncated endoxylanase ORF encoding both the 41 kDa endoxylanase and preceding 32 amino acid residues which were proposed to function as a signal peptide and translation start for the 41 kDa endoxylanase form (Banik, et al., supra) [Sequence ID No. 22].

Plasmid pMC138 contains a transcriptional fusion of the amy-2 promoter (−74/−737; GenBank J04203) to the xyl26 gene, at a unique Msc1 restriction site located downstream of the TATA box of both genes, and includes the full coding region of xyl26 containing introns 1 and 2. The polyadenylation site in the xyl26 gene was fused by overlap extension PCR to the Nos terminator as described for plasmids pMC134/136/137. The plasmids are summarized in Table III below.

TABLE III

Barley endoxylanase expression plasmids

| Plasmid | 5'UTR | Signal Peptide | Endoxylanase ORF | Gene Product (MW) |
|---------|-------|----------------|------------------|-------------------|
| pMC134  | amy-2 | amy-2          | 34 kDa           | 42 kDa            |
| pMC136  | amy-2 | amy-2          | 41 kDa           | 47 kDa            |
| pMC137  | amy-2 | 32aa xyl*      | 41 kDa           | 48 kDa            |
| pMC138  | amy-2 | amy-2          | 62 kDa           | 61.4 kDa          |

* Putative Signal Peptide (Banik, et al., Supra)

Plasmid DNA, 200 μg in 100 μl 10 mM Tris pH 8.0, 0.1 mM EDTA, was incubated for 20 minutes in a 1 ml protoplast suspension combined with 1 ml PEG solution (40%(w/v) PEG 3350 (Sigma), 0.4M mannitol and 0.1M Ca(NO$_3$)$_2$, pH 9.0). Sheared salmon sperm DNA (200 μg) was used for blank transfections.

After incubation, the protoplast suspension was diluted to 12 ml by adding 2 ml aliquots of 0.2M CaCl$_2$. The protoplasts were harvested by centrifugation (5 minutes at 100×g) and resuspended in 1 ml AMP1080 (10 mM MES, 20 mM CaCl$_2$, 0.1M D-glucose, 0.67M mannitol, 0.385% (w/v) Gamborg B5, 10 mM arginine, 50 μg/ml ampicillin, 5 μg/ml nystatin, 10 μM GA$_3$ adjusted to pH 5.4 and 1080 mOsm). The protoplasts were then incubated at 25° C. in the dark in flat bottomed wells.

At defined time points, the protoplasts were harvested from the medium by centrifugation and resuspended in fresh medium, then lysed by 2 cycles of freeze-thaw followed by a 5 second sonification. The samples were centrifuged (5 min at 14000×g) and enzyme activity measured in the supernatant and in the medium from the harvested protoplasts.

Endoxylanase Activity Assay

Standard endoxylanase activity assays were performed, as described above for Example 1, using Birchwood AZCL-xylan (MegaZyme, Australia).

Endoxylanase activity detected in transformed barley aleurone protoplasts is shown in FIGS. 18–20. FIG. 18 shows the total activity detected, namely, the sum of activities found in the protoplasts and the medium. FIG. 19 shows enzyme activity secreted into media, and FIG. 20 shows cellular activity. Endoxylanase activity is expressed as the increase in absorbance at 595 μm per minute per 10$^6$ protoplasts.

In protoplasts transfected with salmon sperm DNA (control), the total endoxylanase activity accumulated during the incubation period (FIG. 18). FIG. 19 shows that much of the endoxylanase activity in the control protoplasts (endogenous barley endoxylanase) is secreted into the medium around the protoplasts.

Figure 20A:
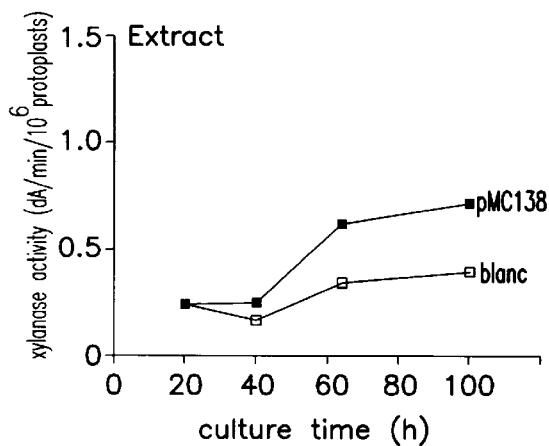
FIGS. 20(A–B) is a graph showing a time course of endoxylanase activity detected within barley aleurone protoplasts transformed with either pMC 138 (FIG. 20A) or with pMC134, pMC136 or pMC137 (FIG. 20B) with reference to untransformed protoplasts as a control (blanc).
Figure 20B:
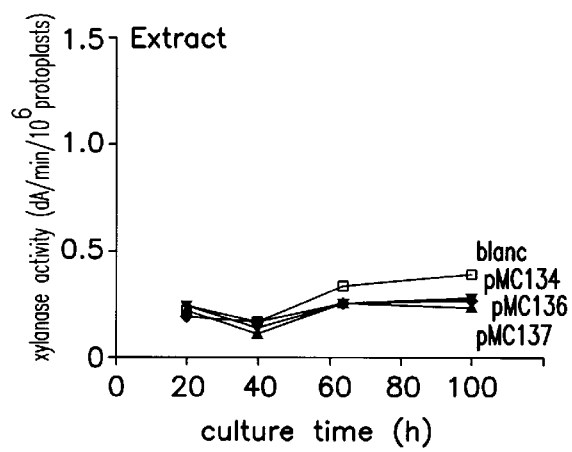
Figure 19A:
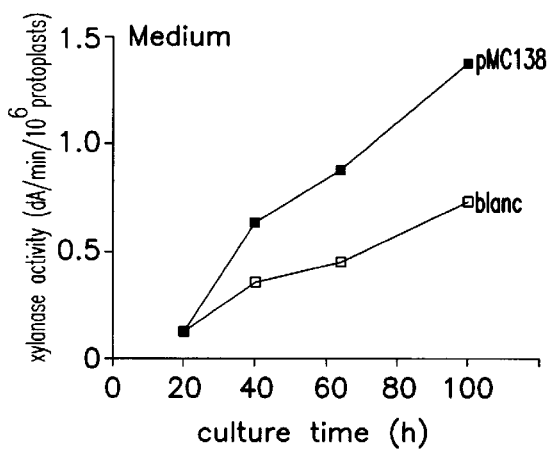
FIGS. 19(A–B) is a graph showing a time course of endoxylanase activity detected in the assay medium of barley aleurone protoplasts transformed with either pMC138 (FIG. 19A) or with pMC134, pMC136 or pMC137 (FIG. 19B) with reference to untransformed protoplasts as a control (blanc).
Figure 19B:
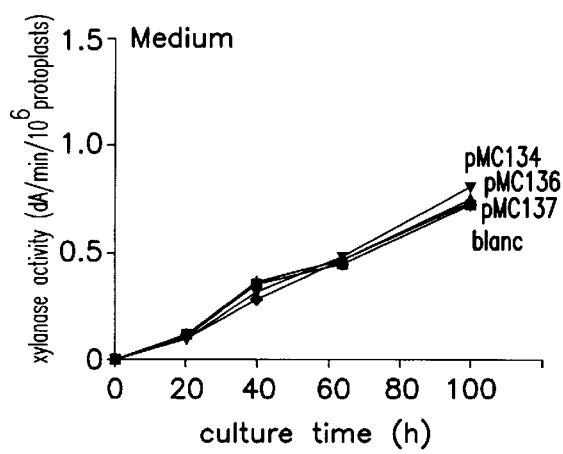
Figure 18A:
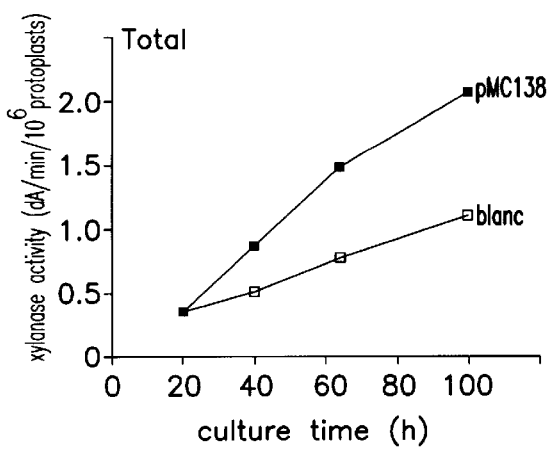
FIGS. 18(A–B) is a graph showing a time course of total endoxylanase activity expressed by barley aleurone protoplasts transformed with either the full length xyl26 gene (pMC138) (FIG. 18A) or truncations of the xyl cDNA (pMC134, pMC136 and pMC137) (FIG. 18B), with reference to untransformed protoplasts as a control (blanc).
Figure 18B:
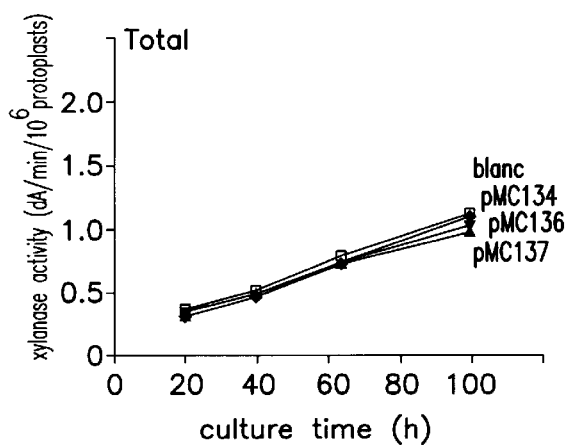

In FIGS. 18A, 19A and 20A, the endoxylanase activity of cells transformed with the full length 61.4 kDa genomic coding sequence is compared with the control. In FIGS. 18B, 19B and 20B, the endoxylanase activity of cells transformed with the truncated forms of the coding sequence are compared with the control.

The data show endoxylanase activity was increased at least 2 fold by transformation with the full length gene (pMC138), while no other gene construct increased expression of endoxylanase activity. Most of the enzyme activity was secreted.

This data indicates that the synthesis of active barley endoxylanase requires expression of the full-length, 62 kDa precursor polypeptide, and that amino acid sequences in the N-terminal region, upstream of the 42 kDa and the 34 kDa endoxylanase forms, are essential for expression of active enzyme.

0

We claim:

1. An isolated nucleic acid sequence comprising a coding sequence for a barley endoxylanase protein of approximately 62 kDa, or variations of the nucleic acid sequence permitted by genetic code degeneracy.

2. The isolated nucleic acid sequence of claim 1 encoding the amino acid sequence of Sequence ID No. 2.

3. The nucleic acid sequence of claim 1, further comprising Intron 1, spanning nucleotides 1895 to 1977 of Sequence ID No.1, Intron 2, spanning nucleotides 2500 to 2590 of Sequence ID No. 1, or both.

4. The nucleic acid sequence of claim 1, comprising the coding sequence spanning nucleotides 1877 to 3721 of Sequence ID No. 1.

5. An isolated nucleic acid sequence encoding a barley endoxylanase protein of approximately 62 kDa or variations of the nucleic acid sequence permitted by genetic code degeneracy, having at least one codon modified according to optimal codon frequencies for a particular cellular host.

6. A nucleic acid construct comprising the nucleic acid sequence of claim 1.

7. The construct of claim 6, comprising Intron 1, spanning nucleotides 1895 to 1977 of Sequence ID No.1, Intron 2, spanning nucleotides 2500 to 2590 of Sequence ID No. 1, or both.

8. A nucleic acid construct comprising a coding sequence for a barley endoxylanase protein of approximately 62 kDa, or variations of the nucleic acid sequence permitted by genetic code degeneracy; and a heterologous signal peptide.

9. A nucleic acid construct comprising a coding sequence for a barley endoxylanase protein of approximately 62 kDa, or variations of the nucleic acid sequence permitted by genetic code degeneracy; and a heterologous promoter sequence.

10. The construct of claim 9, wherein the promoter comprises a cereal seed-specific promoter.

11. The construct of claim 9, wherein the promoter comprises an aleurone specific promoter.

12. The construct of claim 9, wherein the promoter comprises an early promoter.

13. The construct of claim 9, wherein the promoter comprises an α-amylase promoter.

14. The construct of claim 9, wherein the promoter comprises an α amylase promoter, Gbl2 promoter, EPB1 promoter or EPB2 promoter.

15. The construct of claim 14, wherein the promoter comprises a high pI α amylase promoter.

16. A host cell transformed with the nucleic acid sequence of claim 1 encoding 62 kDa barley endoxylanase.

17. The host cell of claim 16, wherein said host cell is a bacterial, yeast, plant, or animal cell.

18. A plant cell transformed with the nucleic acid sequence of claim 1 encoding 62 kDa barley endoxylanase.

19. The plant cell of claim 18, transformed with the coding sequence of Sequence ID No. 1.

20. The plant cell of claim 18, wherein the nucleic acid sequence comprises Intron 1, spanning nucleotides 1895 to 1977 of Sequence ID No.1, Intron 2, spanning nucleotides 2500 to 2590 of Sequence ID No. 1, or both.

21. The plant cell of claim 18, wherein the nucleic acid sequence further encodes a heterologous signal peptide.

22. The plant cell of claim 18, wherein the nucleic acid sequence further comprises a heterologous promoter sequence.

23. The plant cell of claim 22, wherein the heterologous promoter comprises a cereal seed-specific promoter.

24. The plant cell of claim 23, wherein the cereal seed-specific promoter comprises an aleurone specific promoter.

25. The plant cell of claim 22, wherein the promoter comprises an early promoter.

26. The plant cell of claim 25, wherein the promoter comprises an α amylase promoter, Gblpromoter, EPB1 promoter, or EPB2 promoter.

27. The plant cell of claim 26, wherein the promoter comprises an α-amylase promoter.

28. The plant cell of claim 27, wherein the promoter comprises a high pI α amylase promoter.

29. A transformed plant cell comprising the nucleic acid sequence of claim 1 encoding endoxylanase operably linked to a strong aleurone-specific promoter, active from an early stage of germination and malting.

30. A method for enhancing endoxylanase production in a plant cell, the method comprising:

transforming a plant cell with the nucleic acid sequence of claim 1 encoding 62 kDa barley endoxylanase, wherein the nucleic acid sequence is operably linked to a promoter to induce enhanced transcription of endoxylanase in the plant cell.

31. The method of claim 30, wherein the promoter is a seed-specific promoter.

32. The method of claim 30, wherein the promoter is an endosperm-specific promoter expressed during grain development.

33. A method of degrading xylan in a plant, the method comprising:

transforming a plant with the nucleic acid sequence of claim 1 encoding 62 kDa barley endoxylanase, wherein the nucleic acid sequence is operably linked to a promoter to induce enhanced transcription of endoxylanase.

34. The method of claim 33, wherein the promoter induces expression of endoxylanase in the host cell.

35. The method of claim 33, wherein the promoter comprises a cereal grain specific promoter.

36. The method of claim 35, wherein the promoter comprises an α-amylase promoter.

37. A method for producing active endoxylanase comprising:

transforming a host cell with the nucleic acid sequence of claim 2 encoding a 62 kDa barley endoxylanase; and expressing the endoxylanase in the host cell.

38. The method of claim 37, wherein the host cell is a bacterial, yeast, or plant cell.

* * * * *

UNITED STATES PATENT AND TRADEMARK OFFICE
CERTIFICATE OF CORRECTION

PATENT NO.   : 6,031,155
DATED        : February 29, 2000
INVENTOR(S)  : Cameron-Mills et al.

It is certified that error appears in the above-identified patent and that said Letters Patent is hereby corrected as shown below:

Column 9,
Line 21: "hor3" should read -- hor1 --

Column 10,
Line 5: "1:1 15-122" should read -- 1:115-122 --

Column 19,
Line 64: "Southern Blotting" should be a heading; "Southern Blot" should start a new paragraph.

Column 22,
Line 28, " 595 um" should read -- 595 nm --

Column 52,
Line 9, claim 26: "Gblpromoter" should read -- Gbl promoter --

Signed and Sealed this

Twenty-first Day of August, 2001

*Attest:*

*Attesting Officer*

NICHOLAS P. GODICI
*Acting Director of the United States Patent and Trademark Office*